(12) United States Patent
Yamaguchi et al.

(10) Patent No.: US 8,169,471 B2
(45) Date of Patent: May 1, 2012

(54) IMAGE CAPTURING SYSTEM, IMAGE CAPTURING METHOD, AND COMPUTER READABLE MEDIUM

(75) Inventors: Hiroshi Yamaguchi, Ashigarakami-gun (JP); Kiyohiro Maeda, Ashigarakami-gun (JP); Hideyasu Ishibashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 643 days.

(21) Appl. No.: 12/267,328

(22) Filed: Nov. 7, 2008

(65) Prior Publication Data

US 2009/0122152 A1 May 14, 2009

(30) Foreign Application Priority Data

Nov. 9, 2007 (JP) .................................. 2007-292507
Oct. 21, 2008 (JP) .................................. 2008-271366

(51) Int. Cl.
*H04N 7/18* (2006.01)
(52) U.S. Cl. ........................... 348/70; 348/269; 348/370
(58) Field of Classification Search .................... 348/65, 348/68, 69, 164, 266, 272, 273, 277–280, 348/370, 371, 268, 269
See application file for complete search history.

(56) References Cited

U.S. PATENT DOCUMENTS

| | | | | |
|---|---|---|---|---|
| RE34,411 E | * | 10/1993 | Nishioka et al. | ................. 348/70 |
| 6,471,636 B1 | * | 10/2002 | Sano et al. | .................... 600/109 |
| 6,800,057 B2 | * | 10/2004 | Tsujita et al. | ................. 600/160 |
| 7,330,749 B1 | | 2/2008 | Bhunachet | |
| 7,612,822 B2 | * | 11/2009 | Ajito et al. | ..................... 348/336 |
| 7,667,180 B2 | * | 2/2010 | Maeda | ........................ 250/208.1 |
| 2003/0176768 A1 | * | 9/2003 | Gono et al. | .................... 600/109 |
| 2004/0186351 A1 | | 9/2004 | Imaizumi et al. | |
| 2006/0247535 A1 | | 11/2006 | Sendai | |
| 2006/0251408 A1 | * | 11/2006 | Konno et al. | .................... 396/14 |
| 2007/0064119 A1 | * | 3/2007 | Komiya et al. | ............ 348/222.1 |
| 2007/0073104 A1 | * | 3/2007 | Iketani et al. | ................. 600/109 |

FOREIGN PATENT DOCUMENTS

| | | |
|---|---|---|
| EP | 1 302 152 A1 | 4/2003 |
| WO | 00/54652 A1 | 9/2000 |

OTHER PUBLICATIONS

EP Communication, dated Mar. 20, 2009, issued in corresponding EP Application No. 08019508.4, 5 pages.

* cited by examiner

*Primary Examiner* — Nhan T Tran
*Assistant Examiner* — Chriss Yoder, III
(74) *Attorney, Agent, or Firm* — Sughrue Mion, PLLC

(57) ABSTRACT

Provided is an image capturing system including an image capturing section that includes a plurality of first light receiving elements for receiving light of a first wavelength region and a plurality of second light receiving elements for receiving light of a second wavelength region, a control section that causes to be generated, from a subject, light of a different spectrum at a different timing for each of the first wavelength region and the second wavelength region, and an image generating section that generates an image from light of a first spectrum from the subject received by the first light receiving elements at a predetermined timing, and light of a second spectrum from the subject received by the second light receiving elements at a timing other than the predetermined timing.

16 Claims, 11 Drawing Sheets

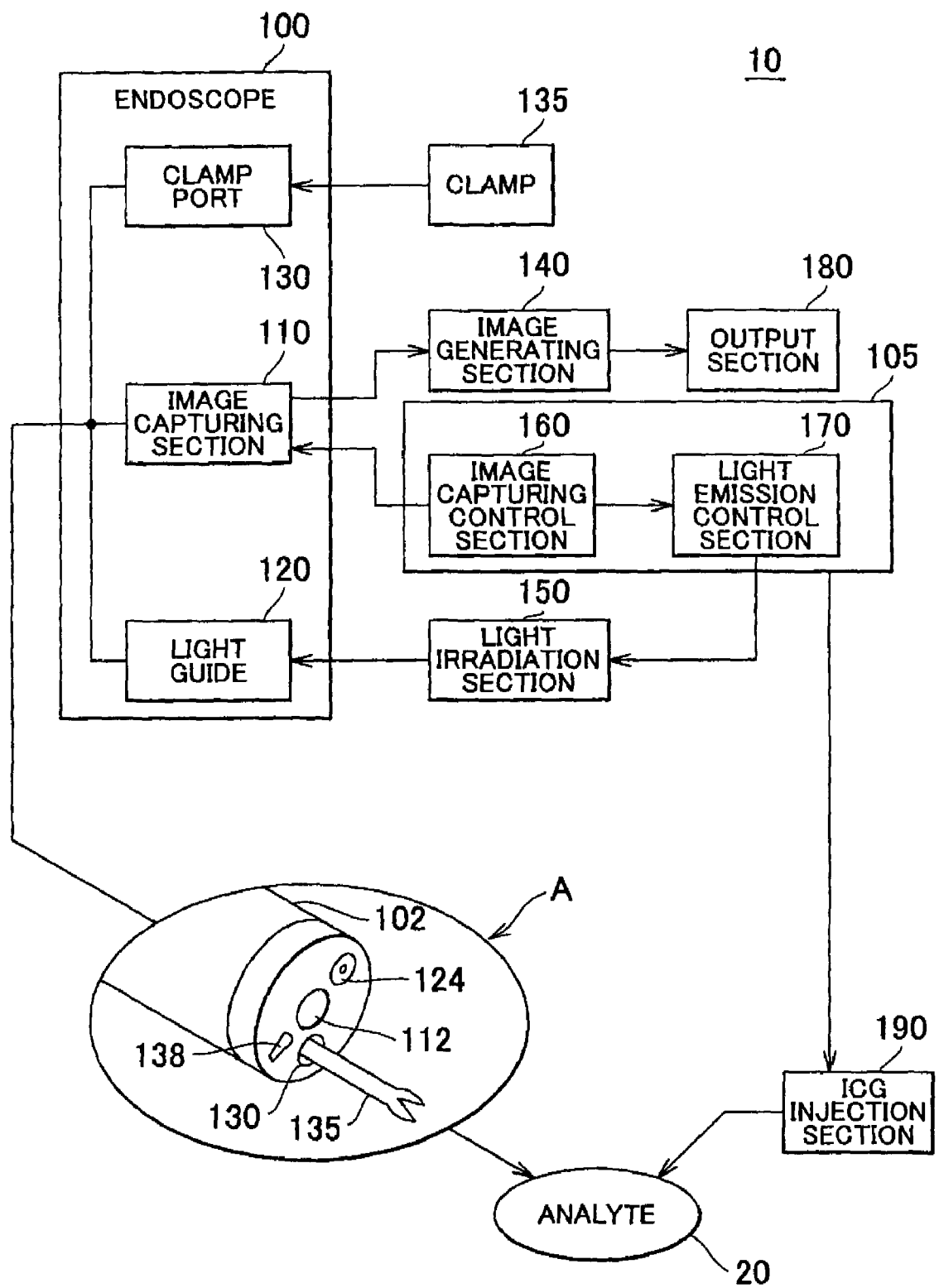
F I G . 1

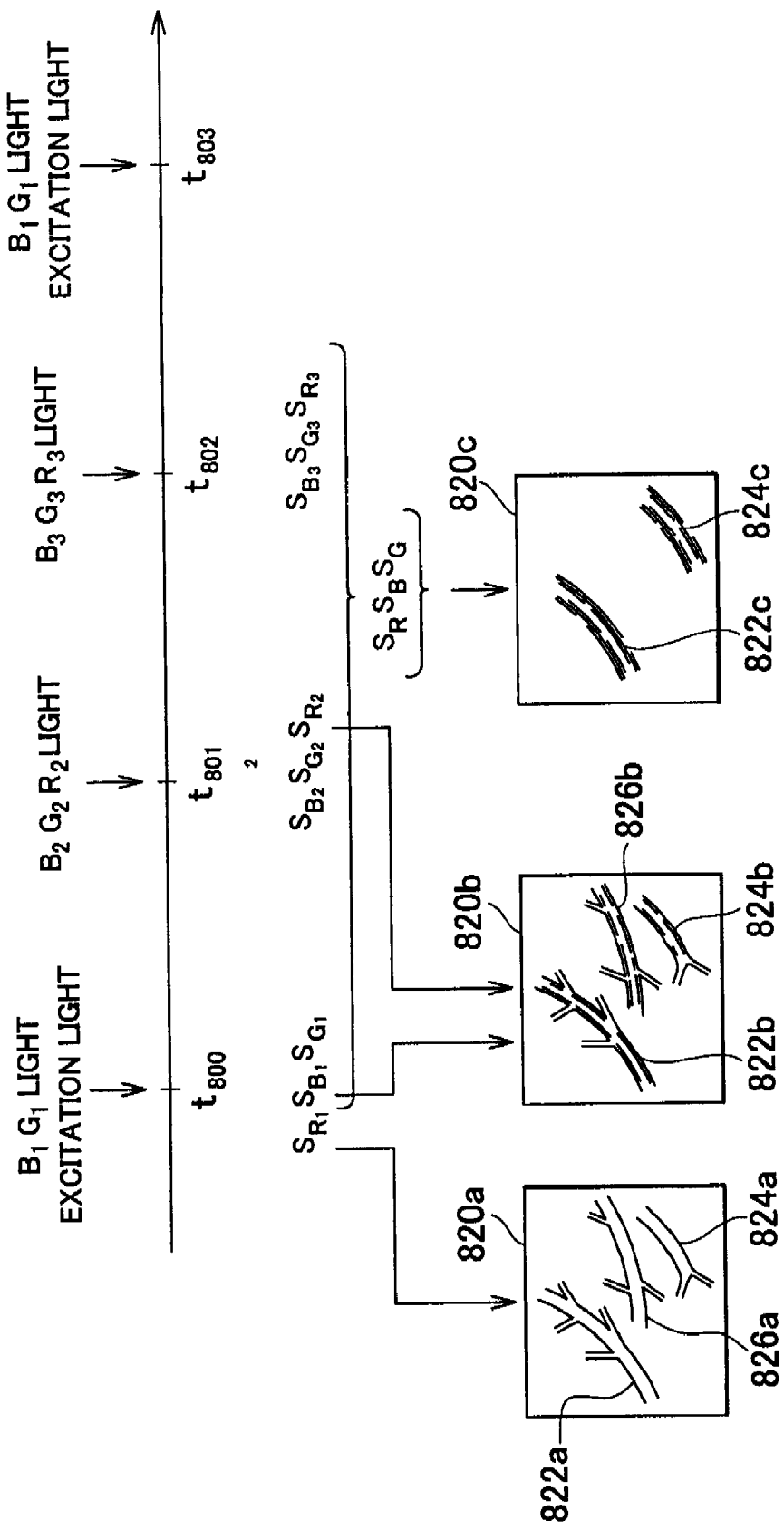
F I G. 10

IMAGE CAPTURING SYSTEM, IMAGE CAPTURING METHOD, AND COMPUTER READABLE MEDIUM

CROSS REFERENCE TO RELATED APPLICATION

The present application claims priority from a Japanese Patent Applications No. 2007-292507 filed on Nov. 9, 2007 and No. 2008-271366 filed on Oct. 21, 2008, the contents of which are incorporated herein by reference.

BACKGROUND

1. Technical Field

The present invention relates to an image capturing system, an image capturing method, and a computer readable medium storing thereon a program. In particular, the present invention relates to an image capturing system, an image capturing method for capturing an image, and a computer readable medium for storing thereon a program used in the image capturing system.

2. Description of the Related Art

An electronic endoscope system capable of capturing an image of tissues to be observed existing under an living organism is known, for example by Japanese Patent Application Publication No. 2007-54113. In addition, an image capturing apparatus that captures an optical image based on re-radiation light emitted from a portion to be observed in response to irradiation of light thereto is also known, for example as disclosed in Japanese Patent Application Publication No. 2002-345733.

SUMMARY

Based on the technology of Japanese Patent Application Publication No. 2007-54113, it is impossible to capture a visible light image with high sensitivity, since there are a plurality of B pixels for receiving light from different wavelength regions. In addition, based on the invention of Japanese Patent Application Publication No. 2002-345733, it is impossible to obtain an image of a narrow bandwidth. According to both of the above prior art technologies, it is impossible to provide an image of a desirable bandwidth and an image to be observed, by a simple configuration.

In view of the above, according to an aspect of the innovations herein, provided is an image capturing system including: an image capturing section that includes a plurality of first light receiving elements for receiving light of a first wavelength region and a plurality of second light receiving elements for receiving light of a second wavelength region; a control section that causes light of a different spectrum at a different timing for each of the first wavelength region and the second wavelength region; and an image generating section that generates a first image from a combination that includes at least one of light of a first spectrum from the subject received by the plurality of first light receiving elements at a predetermined timing, light of a second spectrum from the subject received by the plurality of second light receiving elements at the predetermined timing, light of a third spectrum from the subject received by the plurality of first light receiving elements at a timing other than the predetermined timing, and light of a fourth spectrum from the subject received by the plurality of second light receiving elements at the timing other than the predetermined timing, and generates a second image from a combination different from the combination used to generate the first image.

An arrangement is possible in which the control section causes to be generated, from the subject, light of a first partial wavelength region included in the first wavelength region and light of a second partial wavelength region included in the second wavelength region, and causes to be generated, from the subject, light of a third partial wavelength region included in the first wavelength region and light of a fourth partial wavelength region included in the second wavelength region, and the image generating section generates the first image from a combination that includes at least one of light of the first partial wavelength region from the subject received by the plurality of first light receiving elements at the predetermined timing, the light of the third partial wavelength region from the subject received by the plurality of first light receiving elements at the timing other than the predetermined timing, the light of the second partial wavelength region from the subject received by the plurality of second light receiving elements at the predetermined timing, and the light of the fourth partial wavelength region from the subject received by the plurality of second light receiving elements at the timing other than the predetermined timing, and generates the second image from a combination different from the combination used to generate the first image.

The image capturing system may further include a light emission section that causes to emit, from the subject, light of the first partial wavelength region, the second partial wavelength region, the third partial wavelength region, and the fourth partial wavelength region, where the control section controls the light emission section to emit the light of the first partial wavelength region and the light of the second partial wavelength region from the subject at the predetermined timing, and that controls the light emission section to emit the light of the third partial wavelength region and the light of the fourth partial wavelength region from the subject at the timing other than the predetermined timing.

An arrangement is possible in which the light emission section emits the light of the first partial wavelength region, the second partial wavelength region, the third partial wavelength region, and the fourth partial wavelength region, the control section controls the light emission section to emit the light of the first partial wavelength region and the light of the second partial wavelength region towards the subject at the predetermined timing, and that controls the light emission section to emit the light of the third partial wavelength region and the light of the fourth partial wavelength region towards the subject at the timing other than the predetermined timing, at the predetermined timing, the plurality of first light receiving elements receive the light of the first partial wavelength region reflected from the subject, and the plurality of second light receiving elements receive the light of the second partial wavelength region reflected from the subject, and at the timing other than the predetermined timing, the plurality of first light receiving elements receive the light of the third partial wavelength region reflected from the subject, and the plurality of second light receiving elements receive the light of the fourth partial wavelength region reflected from the subject.

An arrangement is possible in which the image generating section generates a composite image by combining the first image and the second image. An arrangement is possible in which the image generating section generates the second image representing an image of the subject, from the light of the first partial wavelength region received by the plurality of first light receiving elements at the predetermined timing, the light of the third partial wavelength region received by the plurality of first light receiving elements at the timing other than the predetermined timing, the light of the second partial wavelength region received by the plurality of second light receiving elements at the predetermined timing, and the light of the fourth partial wavelength region received by the plurality of second light receiving elements at the timing other than the predetermined timing.

The image generating section may generate a composite image by overlapping the first image onto the second image with an emphasis on the first image. The image capturing system may further include an output section that outputs the first image and the second image generated by the image generating section, in association with each other.

The image generating section may generate the second image based on a summation, for each first light receiving element, of an amount of light of the first partial wavelength region received by the plurality of first light receiving elements at the predetermined timing and an amount of light of the third partial wavelength region received by the plurality of first light receiving elements at the timing other than the predetermined timing, and on a summation, for each second light receiving element, of an amount of light of the second partial wavelength region received by the plurality of second light receiving elements at the predetermined timing and an amount of light of the fourth partial wavelength region received by the plurality of second light receiving elements at the timing other than the predetermined timing.

An arrangement is possible in which the plurality of first light receiving elements and the plurality of second light receiving elements receive the light emitted by the light emission section after being reflected from an object existing inside a substance, the plurality of first light receiving elements receive the light of the first wavelength region that is shorter than the second wavelength region, the control section controls the light emission section to emit the light of the first partial wavelength region and of the second partial wavelength region that are shorter than the third partial wavelength region, at the predetermined timing, and the image generating section generates the first image representing an image of an object existing at a shallower position from a surface of the substance based at least on the light of the first partial wavelength region received by the plurality of first light receiving elements at the predetermined timing.

An arrangement is possible in which the control section controls the light emission section to emit the light of the first partial wavelength region shorter than the third partial wavelength region and the light of the second partial wavelength region longer than the fourth partial wavelength region, at the predetermined timing, and the image generating section generates the first image representing an image of an object existing at a shallower position from the surface of the substance and an object existing at a deeper position from the surface of the substance, based at least on the light of the first partial wavelength region received by the plurality of first light receiving elements at the predetermined timing and the light of the second partial wavelength region received by the plurality of second light receiving elements at the predetermined timing.

An arrangement is possible in which the plurality of first light receiving elements and the plurality of second light receiving elements receive the light emitted by the light emission section after being reflected from an object existing inside a substance, the plurality of first light receiving elements receive the light of the first wavelength region that is longer the second wavelength region, the control section controls the light emission section to emit the light of the first partial wavelength region and of the second partial wavelength region that are longer than the third partial wavelength region, at the predetermined timing, and the image generating section generates the first image representing an image of an object existing at a deeper position from a surface of the substance based at least on the light of the first partial wavelength region received by the plurality of first light receiving elements at the predetermined timing.

The image capturing system may further include a first spectral filter that transmits the light of the first partial wavelength region and the light of the third partial wavelength region; and a second spectral filter that transmits the light of the second partial wavelength region and the light of the fourth partial wavelength region, where the plurality of first light receiving elements receive light from the subject after being transmitted through the first spectral filter, and the plurality of second light receiving elements receive light from the subject after being transmitted through the second spectral filter.

An arrangement is possible in which the light emission section includes a plurality of light emitting elements that respectively emit light of a different spectrum from each other, and the control section controls the light emission at the predetermined timing and at the timing other than the predetermined timing by controlling respective light emission intensities of the plurality of light emitting elements.

The image capturing system may further include an irradiation light filter that transmits the light of the first partial wavelength region and the light of the second partial wavelength region, where the light emission section emits light of a wavelength region, the wavelength region including the first partial wavelength region, the second partial wavelength region, and at least one of the third partial wavelength region and the fourth partial wavelength region, and the control section controls the light from the light emission section to irradiate the subject after being transmitted through the irradiation light filter, at the predetermined timing.

An arrangement is possible in which the image generating section includes: a motion specifying section that specifies a motion of an object on an image among the plurality of timings, based on a plurality of images, the plurality of images being generated by the light of the first partial wavelength region received by the plurality of first light receiving elements at a plurality of timings including the predetermined timing and the light of the second partial wavelength region received by the plurality of second light receiving elements at the plurality of timings, and a corrected image generating section that generates a corrected image which is an image of a subject generated by the light of the first partial wavelength region and the light of the second partial wavelength region at the timing other than the predetermined timing, based on the light of the first wavelength region received by the plurality of first light receiving elements at the predetermined timing and the light of the second wavelength region received by the plurality of second light receiving elements at the predetermined timing.

An arrangement is possible in which the image generating section further includes: a subject image generating section that generates the second image based on the corrected image and an image generated by the light of the third partial wavelength region received by the plurality of first light receiving elements at the timing other than the predetermined timing and the light of the fourth partial wavelength region received by the plurality of second light receiving elements at the timing other than the predetermined timing.

An arrangement is possible in which the image capturing section further includes a plurality of third light receiving elements for receiving light of a third wavelength region, the light emission section emits light of the first partial wavelength region, the second partial wavelength region, the third partial wavelength region, the fourth partial wavelength region, and a fifth partial wavelength region and a sixth partial wavelength region included in the third wavelength region, the control section controls the light emission section to emit the light of the first partial wavelength region, the light of the second partial wavelength region, the light of the fifth partial wavelength region to the subject at the predetermined timing, and to emit the light of the third partial wavelength region, the light of the fourth partial wavelength region, and the light of the sixth partial wavelength region to the subject at the timing other than the predetermined timing, at the predetermined timing, the plurality of first light receiving elements receive the light of the first partial wavelength region reflected from the subject, the plurality of second light receiving elements receive the light of the second partial wavelength region reflected from the subject, and the plurality of third light receiving elements receive the light of the fifth partial wavelength region reflected from the subject, and at the timing other than the predetermined timing, the plurality of first light receiving elements receive the light of the third partial wavelength region reflected from the subject, the plurality of second light receiving elements receive the light of the fourth partial wavelength region reflected from the subject, and the third light receiving elements receive the light of the sixth partial wavelength region reflected from the subject, and the image generating section generates a first image from a combination that includes at least one of the light of the first partial wavelength region received by the plurality of first light receiving elements at the predetermined timing, the light of the third partial wavelength region received by the plurality of first light receiving elements at the timing other than the predetermined timing, the light of the second partial wavelength region received by the plurality of second light receiving elements at the predetermined timing, the light of the fourth partial wavelength region received by the plurality of second light receiving elements at the timing other than the predetermined timing, the light of the fifth partial wavelength region received by the plurality of third light receiving elements at the predetermined timing, and the light of the sixth partial wavelength region received by the plurality of third light receiving elements at the timing other than the predetermined timing, and generates a second image from a combination different from the combination used to generate the first image.

An arrangement is possible in which the first wavelength region is a blue wavelength region, the second wavelength region is a red wavelength region, and the third wavelength region is a green wavelength region.

According to a second aspect of the innovations herein, provided is an image capturing method including: image capturing including a plurality of first light receiving elements for receiving light of a first wavelength region and a plurality of second light receiving elements for receiving light of a second wavelength region; controlling to cause, to be generated from a subject, light of a different spectrum at a different timing for each of the first wavelength region and the second wavelength region; image generating to generate a first image from a combination that includes at least one of light of a first spectrum from the subject received by the plurality of first light receiving elements at a predetermined timing, light of a second spectrum from the subject received by the plurality of second light receiving elements at the predetermined timing, light of a third spectrum from the subject received by the plurality of first light receiving elements at a timing other than the predetermined timing, and light of a fourth spectrum from the subject received by the plurality of second light receiving elements at the timing other than the predetermined timing, and to generate a second image from a combination different from the combination used to generate the first image.

According to a third aspect of the innovations herein, provided is a computer readable medium storing thereon a program for an image capturing system, the program functioning the image capturing system as: an image capturing section that includes a plurality of first light receiving elements for receiving light of a first wavelength region and a plurality of second light receiving elements for receiving light of a second wavelength region; a control section that causes to be generated, from a subject, light of a different spectrum at a different timing for each of the first wavelength region and the second wavelength region; and an image generating section that generates a first image from a combination that includes at least one of light of a first spectrum from the subject received by the plurality of first light receiving elements at a predetermined timing, light of a second spectrum from the subject received by the plurality of second light receiving elements at the predetermined timing, light of a third spectrum from the subject received by the plurality of first light receiving elements at a timing other than the predetermined timing, and light of a fourth spectrum from the subject received by the plurality of second light receiving elements at the timing other than the predetermined timing, and generates a second image from a combination different from the combination used to generate the first image.

The summary of the invention does not necessarily describe all necessary features of the present invention. The present invention may also be a sub-combination of the features described above.

BRIEF DESCRIPTION OF THE DRAWINGS

FIG. 1 shows an exemplary configuration of an image capturing system 10 of the present embodiment, together with an analyte 20.

FIG. 10 shows an example of an image capturing timing of the image capturing section 110 and an image generated by an image generating section 140.

DESCRIPTION OF EXEMPLARY EMBODIMENTS

Figure 2:
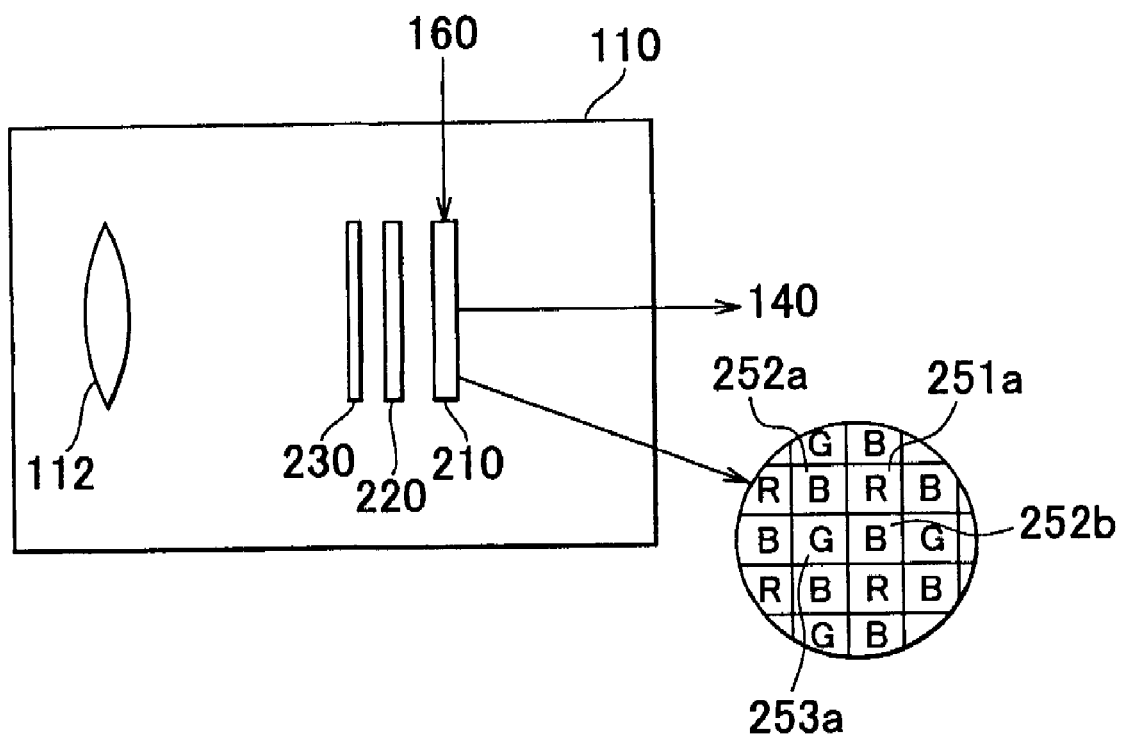
FIG. 2 shows an exemplary configuration of an image capturing section 110.

The invention will now be described based on the preferred embodiments, which do not intend to limit the scope of the present invention, but exemplify the invention. All of the features and the combinations thereof described in the embodiment are not necessarily essential to the invention.

FIG. 1 shows an exemplary configuration of an image capturing system 10 of the present embodiment, together with an analyte 20. The image capturing system 10 includes an endoscope 100, an image generating section 140, an output section 180, a control section 105, a light irradiation section 150, and an ICG injection section 190. Note that Section A in FIG. 1 is an enlarged view of a tip 102 of the endoscope 100.

The ICG injection section 190 injects, to the analyte 20 which is an example of a subject, indocyanine green (ICG) which is a luminescence substance. Although ICG is used as a luminescence substance in the present embodiment, a fluorescent substance other than ICG may also be used as a luminescence substance.

ICG emits fluorescence of a broad spectrum centering around 810 nm, by being excited by infrared light of a wavelength of 750 nm for example. When the analyte 20 is a living organism, the ICG injection section 190 injects ICG to the blood vessels of the living organism by means of intravenous injection. The image capturing system 10 captures the image of the blood vessels within the living organism using luminescence light from the ICG. Note that the luminescence light is one example of light in a specific wavelength region, and includes fluorescence and phosphor. Note that the luminescence light which is an example of light from a subject includes luminescence light of chemical luminescence, triboluminescence, and thermal luminescence, other than light luminescence of excitation light.

The ICG injection section 190 injects ICG to the analyte 20 so that the ICG concentration within the living organism is maintained substantially constant, by means of control performed by the control section 105 for example. Note that the analyte 20 may be a living organism such as a human body, and the captured image of the analyte 20 is to be processed by the image capturing system 10. Note that an object such as a blood vessel exists in the analyte 20.

The endoscope 100 includes an image capturing section 110, a light guide 120, and a clamp port 130. The tip 102 of the endoscope 100 is provided with an objective lens 112 as part of the image capturing section 110. The tip 102 is also provided with an outlet 124 as part of the light guide 120. The tip 102 of the endoscope 100 is provided with a nozzle 138.

A clamp 135 is inserted into the clamp port 130, and the clamp port 130 guides the clamp 135 towards the tip 102. Note that the form of the tip of the clamp 135 may be varied. Various types of treatment equipment may be inserted into the clamp port 130 other than a clamp, for the purpose of treating a living organism. The nozzle 138 sends out water or air.

The light irradiation section 150 generates light to be irradiated from the tip 102 of the endoscope 100. The light generated by the light irradiation section 150 includes infrared light which is an example of excitation light of a wavelength region capable of exciting the luminescence substance included in the analyte 20 thereby causing light of the specific wavelength region, and irradiation light that irradiates the analyte 20. The irradiation light includes component light of R component, G component, and B component.

The light guide 120 is formed by an optical fiber for example. The light guide 120 guides light generated in the light irradiation section 150 to the tip 102 of the endoscope 100. The light guide 120 may include an outlet 124 provided on the tip 102. The light generated in the light irradiation section 150 is irradiated onto the analyte 20 through the outlet 124.

The image capturing section 110 receives at least one of light emitted from the luminescence substance and reflection light resulting from reflection of the irradiation light at the object. The image generating section 140 generates an image by processing light reception data acquired from the image capturing section 110. The output section 180 outputs the image generated by the image generating section 140.

The control section 105 includes an image capturing control section 160 and a light emission control section 170. The image capturing control section 160 controls image capturing of the image capturing section 110. The light emission control section 170 controls the light irradiation section 150 in response to the control by the image capturing control section 160. For example, when the image capturing section 110 captures an image of each component light of infrared light, R component, G component, and B component by time division, the light emission control section 170 controls light irradiated by the light irradiation section 150 onto the analyte 20, so that the timing of irradiation of each component light is synchronized with the image capturing timing.

FIG. 2 shows an exemplary configuration of the image capturing section 110. The image capturing section 110 includes an objective lens 112, an image capturing device 210, a spectral filter 220, and a light reception side excitation light cutting filter 230. The image capturing device 210 includes a plurality of first light receiving elements 251 including a first light receiving element 251a, a plurality of second light receiving elements 252 including a second light receiving element 252a and a second light receiving element 252b, and a plurality of third light receiving elements 253 including a third light receiving element 253a.

The function and the operation of the constituting elements of the image capturing section 110 are explained as follows. In the following explanation, the plurality of first light receiving elements 251 are occasionally collective referred to as a first receiving element 251, the plurality of second light receiving elements 252 are occasionally collectively referred to as a second light receiving element 252, and the plurality of third light receiving elements 253 are occasionally collectively referred to as a third light receiving element 253. In addition, the plurality of first light receiving elements 251, the plurality of second light receiving elements 252, and the plurality of third light receiving elements 253 are occasionally collectively and simply referred to as a light receiving element.

The first light receiving element 251, the second light receiving element 252, and the third light receiving element 253 receive light from a subject provided via the objective lens 112. Specifically, the first light receiving element 251 receives light of a first wavelength region. The second light receiving element 252 receives light of a second wavelength region. The third light receiving section 253 receives light of a third wavelength region that is different from the second wavelength region.

The first wavelength region, the second wavelength region, and the third wavelength region are mutually different wavelength regions, indicating that each of them is a wavelength region that is not included in any of the other wavelength regions. The first light receiving element 251, the second light receiving element 252, and the third light receiving element 253 are arranged two dimensionally in a predetermined pattern.

The spectral filter 220 includes a plurality of filter elements that transmit one of light of the first wavelength region, light of the second wavelength region, and light of the third wavelength region. Each filter element is aligned two dimensionally in association with each of the first light receiving element 251, the second light receiving element 252, and the third light receiving element 253. Each light receiving element receives light transmitted through the corresponding filter element. In this way, the first light receiving element 251, the second light receiving element 252, and the third light receiving element 253 receive light of a different wavelength region from each other.

The light reception side excitation light cutting filter 230 is provided at least between the subject and the second light receiving element 252 and the third light receiving element 253, and cuts light of the wavelength region of excitation light. The second light receiving element 252 and the third light receiving element 253 receive light reflected from the subject via the excitation light cutting filter. In this way, the second light receiving element 252 and the third light receiving element 253 are prevented from receiving the excitation light reflected from the subject.

The light reception side excitation light cutting filter 230 may cut light of the wavelength region of excitation light and light of the specific wavelength region. In this case, the second light receiving element 252 and the third light receiving element 253 are prevented from receiving luminescence light from a subject.

Note that the light reception side excitation light cutting filter 230 may be provided between the subject and the second light receiving element 252. In this case, the light reception side excitation light cutting filter 230 transmits luminescence light.

Just as the spectral filter 220, the light reception side excitation light cutting filter 230 may include filter elements aligned two dimensionally in association with the first light receiving element 251, the second light receiving element 252, and the third light receiving element 253 respectively. The filter element to provide light to the first light receiving element 251 cuts light of the wavelength region of excitation light, and transmits light of the first wavelength region and the specific wavelength region. The filter element to provide light to the second light receiving element 252 cuts light of the wavelength region of excitation light and light of the specific wavelength region, and at least transmits light of the second wavelength region. The filter element to provide light to the third light receiving element 253 cuts light of the wavelength region of excitation light and light of the specific wavelength region, and at least transmits light of the third wavelength region.

The image generating section 140 determines the pixel value of one pixel based at least on the amount of light received by the first light receiving element 251a, the second light receiving element 252a, the second light receiving element 252b, and the third light receiving element 253a. That is, one pixel element is formed by a two dimensional alignment structure of the first light receiving element 251a, the second light receiving element 252a, the second light receiving element 252b, and the third light receiving element 253a, and a plurality of pixel elements are formed by a two dimensional alignment of such pixel element alignment. Note that the light receiving elements may be aligned in any different manner from the alignment structure shown in the present drawing.

Figure 3:
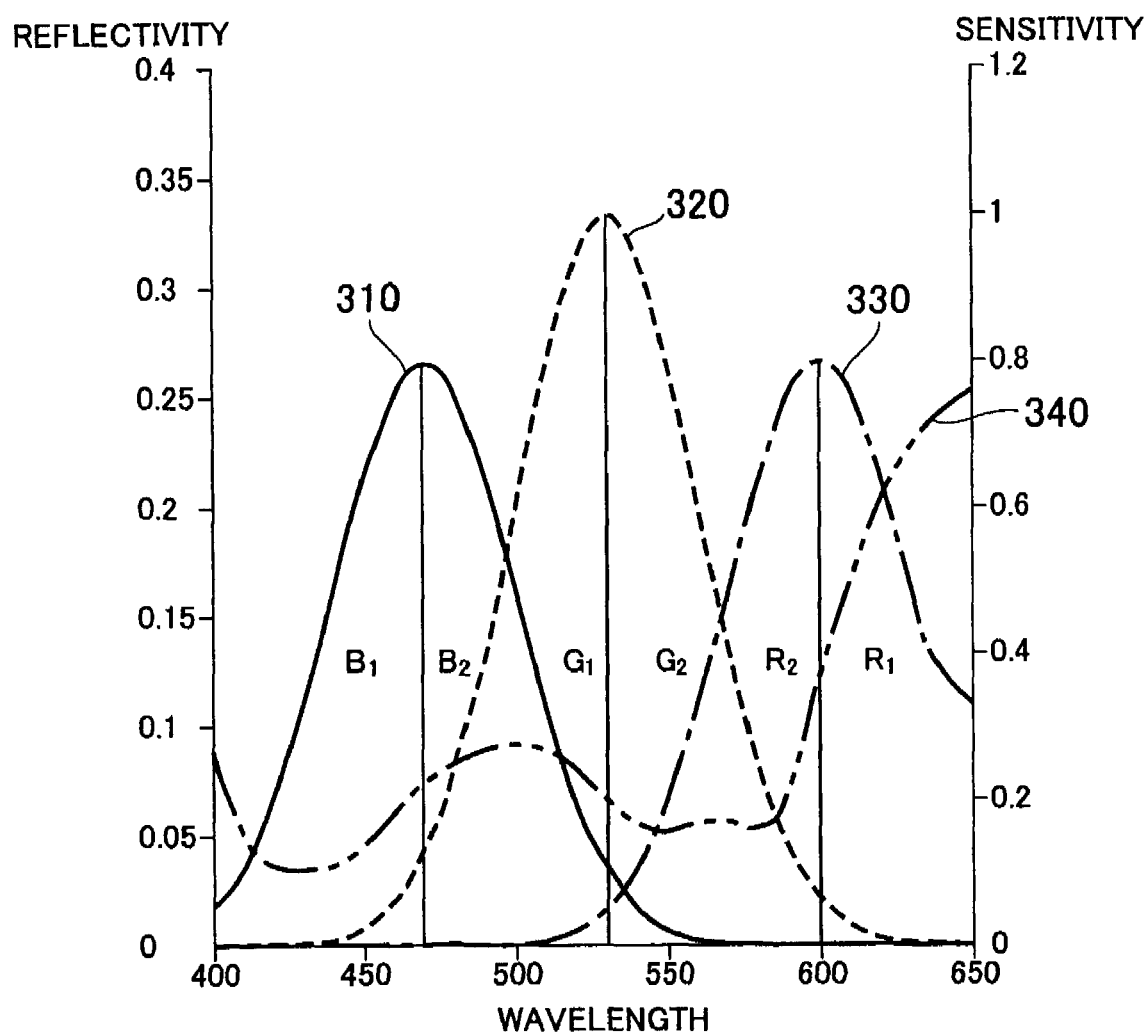
FIG. 3 shows an exemplary spectral sensitivity characteristic of a light receiving element, and an exemplary spectral reflectivity of a surface layer of a living organism that is one example of a target of which the image is to be captured.

FIG. 3 shows an exemplary spectral sensitivity characteristic of a light receiving element, and an exemplary spectral reflectivity of a surface layer of a living organism that is one example of a target of which the image is to be captured. The line 330, the line 310, and the line 320 show the spectral reflectivity distribution of the first light receiving element 251, the second light receiving element 252, and the third light receiving element 253, respectively. The line 340 shows an exemplary spectral reflectivity of a gastrocolic membrana mucosa of which the image is to be captured.

As an example, the first light receiving element 251 is sensitive to the light of a wavelength in the vicinity of 650 nm to which no other light receiving element is sensitive. In addition, the second light receiving element 252 is sensitive to the light of a wavelength in the vicinity of 450 nm to which no other light receiving element is sensitive. In addition, the third light receiving element 253 is sensitive to the light of a wavelength in the vicinity of 550 nm to which no other light receiving element is sensitive.

The first light receiving element 251 is able to receive light of an infrared light region (e.g., 810 nm) which is an example of the specific wavelength region, due to the characteristics of the light reception side excitation light cutting filter 230 and of the spectral filter 220. However, the explanation here is confined to a case where the image capturing system 10 is operated by using the light of a visible light region. A case where the image capturing system 10 is operated by using the light of an infrared light region (e.g., 810 nm) is explained in connection with FIGS. 9 and 10.

In this way, the first light receiving element 251, the second light receiving element 252, and the third light receiving element 253 respectively receive light of R component, light of B component, and light of G component. Note that the first light receiving element 251, the second light receiving element 252, and the third light receiving element 253 may be an image capturing element such as CCD and CMOS, for example. The first light receiving element 251, the second light receiving element 252, and the third light receiving element 253 have a spectral sensitivity characteristic shown by the line 330, the line 310, and the line 320, respectively, due to a combination of the spectral transmission of the light reception side excitation light cutting filter 230, the spectral transmission of the filter element included in the spectral filter 220, and the spectral sensitivity of the image capturing element itself.

The filter element, which includes the filter element included in the spectral filter 220 and the light reception side excitation light cutting filter 230, for supplying light received by the first light receiving element 251 transmits light of a first partial wavelength region (R1) and light of a third partial wavelength region (R2). Note that the filter element functions as a first spectral filter of the present invention. Note that the filter element, which includes the filter element included in the spectral filter 220 and the light reception side excitation light cutting filter 230, for supplying light received by the second light receiving element 252 transmits light of a second partial wavelength region (B1) and light of a fourth partial wavelength region (B2). Note that the filter element functions as a second spectral filter of the present invention. Note that the filter element, which includes the filter element included in the spectral filter 220 and the light reception side excitation light cutting filter 230, for supplying light received by the third light receiving element 253 transmits light of a fifth partial wavelength region (G1) and light of a sixth partial wavelength region (G2).

As an example, the first partial wavelength region (R1) may be 600-630 nm, and the third partial wavelength region (R2) may be 570-600 nm. The second partial wavelength region (B1) may be 440-470 nm, and the fourth partial wavelength region (B2) may be 470-500 nm. The fifth partial wavelength region (G1) may be 500-530 nm, and the sixth partial wavelength region (G2) may be 530-570 nm.

Figure 4:
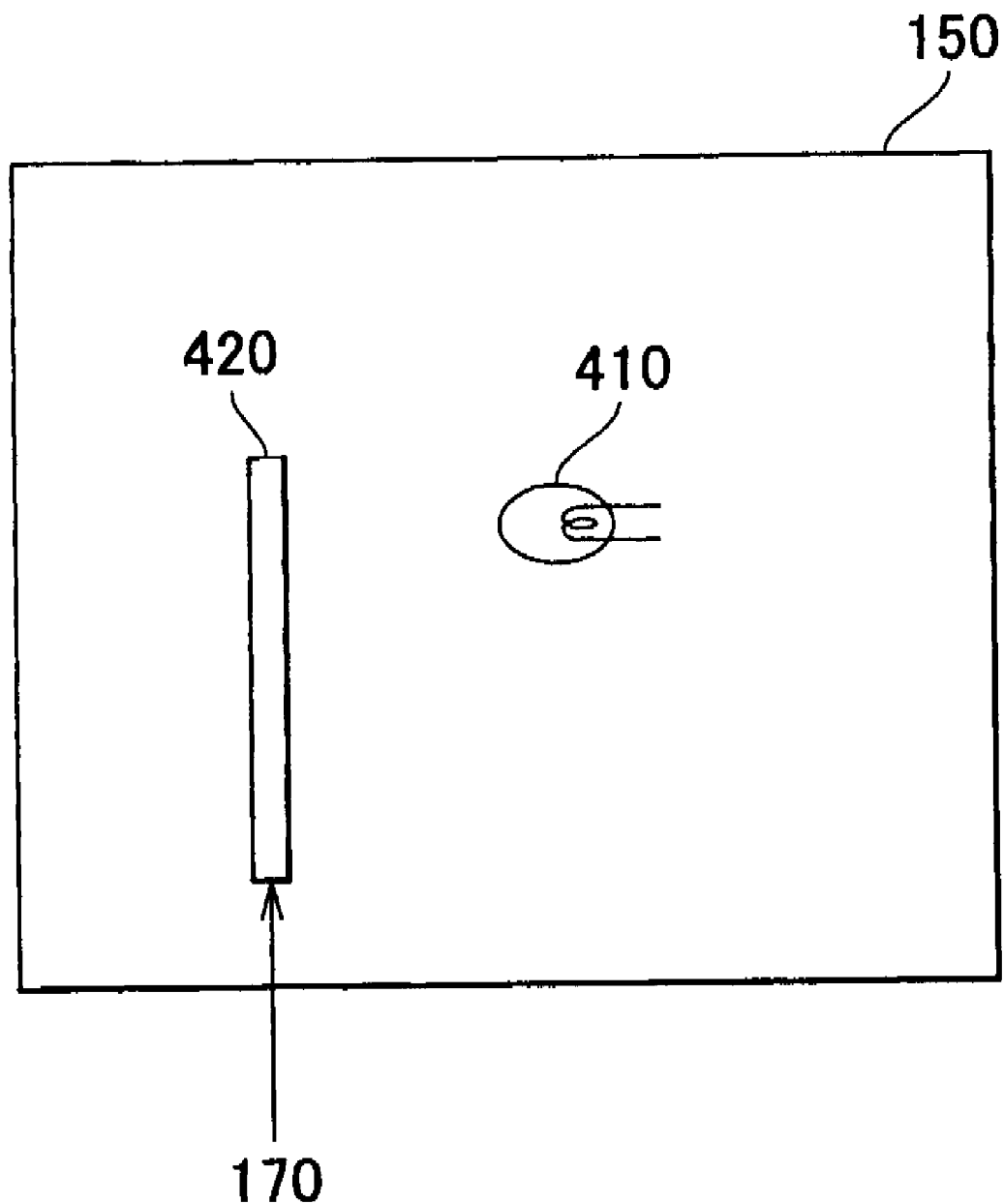
FIG. 4 shows an exemplary configuration of a light irradiation section 150.

FIG. 4 shows an exemplary configuration of a light irradiation section 150. The light irradiation section 150 includes a light emission section 410 and a light source filter 420. The light emission section 410 emits light of a wavelength region that includes a first wavelength region, a second wavelength region, a third wavelength region, a fifth partial wavelength region, and a sixth partial wavelength region. Note that one example of the light emission section 410 in the present embodiment is a xenon lamp.

Figure 5:
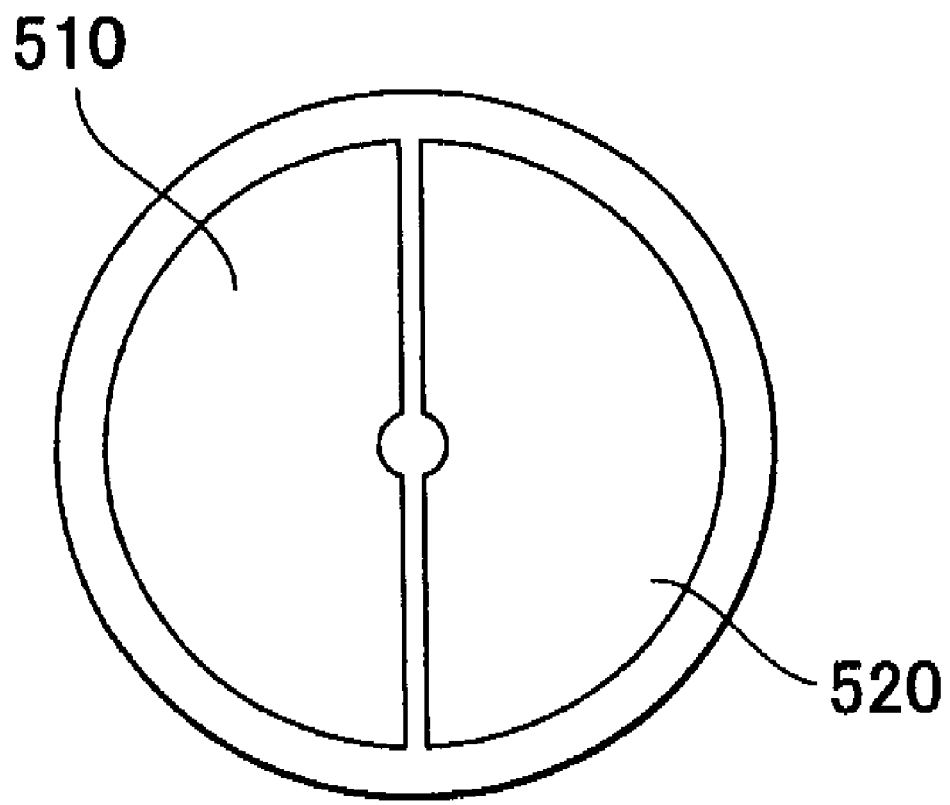
FIG. 5 shows an exemplary configuration of a light source filter 420.

FIG. 5 shows an exemplary configuration of a light source filter 420. FIG. 5 shows a configuration when the light source filter 420 is viewed in the direction of light irradiated onto the light source filter 420 from the light emission section 410. The light source filter 420 includes an irradiation light filter 520 and an irradiation light filter 510. Note that the light emission control section 170 rotates the light source filter 420 on a plane substantially vertical to the direction in which light emitted from the light emission section 410 travels, with its rotation center being the central axis of the light source filter 420.

The irradiation light filter 510 cuts off the light of the third partial wavelength region, the fourth partial wavelength region, and the sixth partial wavelength region, and transmits the light of the first partial wavelength region, the light of the second partial wavelength region, and the fifth partial wavelength region. The irradiation light filter 520 cuts off the light of the first partial wavelength region, the light of the second partial wavelength region, and the fifth partial wavelength region, and transmits the light of the third partial wavelength region, the light of the fourth partial wavelength region, and the sixth partial wavelength region. Note that the light from the light emission section is guided toward a position out of the central axis of the light source filter 420.

Accordingly, at the timing at which the light from the light emission section 410 is guided toward the irradiation light filter 510, the light of the third partial wavelength region, the light of the fourth partial wavelength region, and the light of the sixth partial wavelength region, from among the light from the light emission section 410, are cut off by the irradiation light filter 510, and the light of the first partial wavelength region, the light of the second partial wavelength region, and the light of the fifth partial wavelength region are transmitted through the irradiation light filter 510. Accordingly, at this timing, the light of the first partial wavelength region, the light of the second partial wavelength region, and the light of the fifth partial wavelength region are irradiated onto the subject.

At the timing at which the light from the light emission section 410 is guided towards the irradiation light filter 520, the light of the first partial wavelength region, the light of the second partial wavelength region, and the light of the fifth partial wavelength region, from among the light from the light emission section 410, are cut off by the irradiation light filter 510, and the light of the third partial wavelength region, the light of the fourth partial wavelength region, and the light of the sixth partial wavelength region are transmitted through the irradiation light filter 520. Accordingly, at this timing, the light of the third partial wavelength region, the light of the fourth partial wavelength region, and the light of the sixth partial wavelength region are to be irradiated onto the subject.

Note that the image capturing section 110 receives irradiated light reflected from the analyte 20, at the timing at which the light of the first partial wavelength region, the light of the second partial wavelength region, and the light of the fifth partial wavelength region, being visible light, are irradiated, in response to the control by the image capturing control section 160. Then, the image generating section 140 generates a first visible light image based on the amount of light received by the image capturing section 110. Note that the first visible light image may be an example of the first image in the present invention.

In addition, the image capturing section 110 receives irradiated light reflected from the analyte 20, at the timing at which the light of the third partial wavelength region, the light of the fourth partial wavelength region, and the light of the sixth partial wavelength region, being visible light, are irradiated, in response to the control by the image capturing control section 160. The image generating section 140 generates a second visible light image based on the amount of the light of the first partial wavelength region, the light of the second partial wavelength region, and the reflected light of the fifth partial wavelength region, in addition to the amount of the light of the third partial wavelength region, the light of the fourth partial wavelength region, and the light of the sixth partial wavelength region having been received by the image capturing section 110. Note that the second visible light image may be an example of the second image in the present invention.

Figure 6:
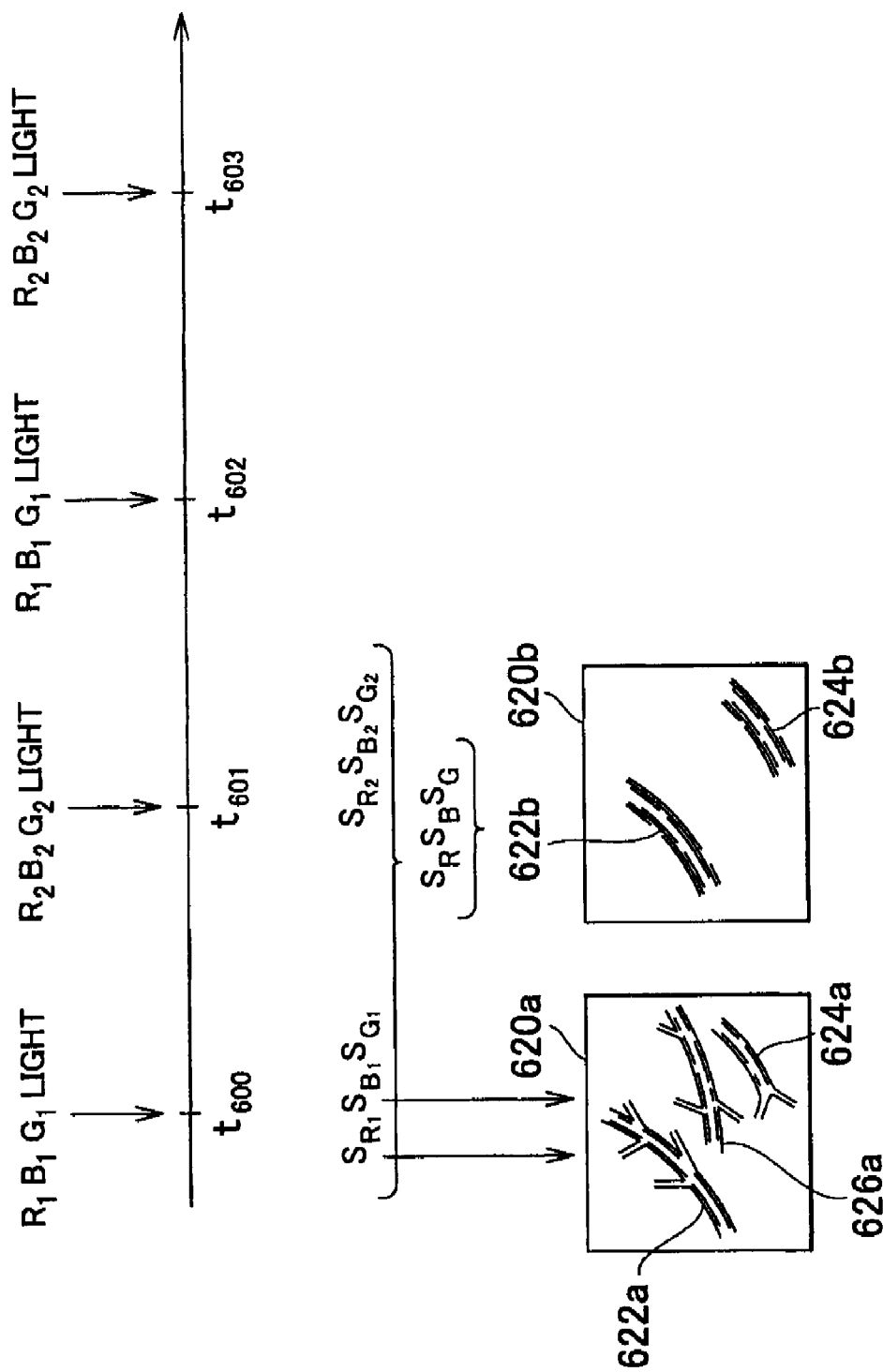
FIG. 6 shows an example of an image capturing timing of the image capturing section 110 and an image generated by an image generating section 140.

FIG. 6 shows an example of an image capturing timing of the image capturing section 110 and an image generated by the image generating section 140. The image capturing control section 160 controls the image capturing section 110 to perform image capturing at the time t600, the time t601, the time t602, the time t603, . . . . In addition, according to the timing control by the image capturing control section 160, the light emission control section 170 controls the light emitted from the light emission section 410 to irradiate the subject via the irradiation light filter 510, at the first timing including the time t600 and the time t602. In this way, the light emission control section 170 controls the light emission section 410 through the irradiation light filter 510 to emit the light of the first partial wavelength region, the light of the second partial wavelength region, and the fifth partial wavelength region towards an subject, by transmitting the light from the light emission section 410. In the present invention, the light of the first partial wavelength region and the light of the second partial wavelength region may be caused by reflection of the light of the first partial wavelength region and the light of the second partial wavelength region at the subject respectively.

Then, at the first timing, the image capturing control section 160 irradiates the light of the wavelength region that includes the first partial wavelength region, the second partial wavelength region, and the fifth wavelength region, to the subject, thereby causing the first light receiving element 251 to receive the light of the first partial wavelength region reflected from the subject, and causing the second light receiving element 252 to receive the light of the second partial wavelength region reflected from the subject, and causing the third light receiving element 253 to receive the light of the third partial wavelength region reflected from the subject. In this way, at the first timing, the image capturing control section 160 controls the first light receiving element 251 to receive the light of the first partial wavelength region from the subject, controls the second light receiving element 252 to receive the light of the second partial wavelength region from the subject, and controls the third light receiving element 253 to receive the light of the third partial wavelength region from the subject.

In addition, at the second timing that includes the time t602, the light emission control section 170 irradiates the light emitted from the light emission section 410 to the subject via the irradiation light filter 520, by timing control by the image capturing control section 160. In this way, at a timing other than a predetermined timing, the light emission control section 170 controls the light emission section 410 to emit the light of the third partial wavelength region, the light of the fourth partial wavelength region, and the light of the sixth partial wavelength region to the subject, by transmitting the light from the light emission section 410 through the irradiation light filter 520. In the present invention, the light of the third partial wavelength region and the light of the fourth partial wavelength region may be caused by reflection of the light of the third partial wavelength region and the light of the fourth partial wavelength region at the subject respectively.

Then at the second timing, the image capturing control section 160 controls the first light receiving element 251 to receive the light of the third partial wavelength region reflected from the subject, controls the second light receiving element 252 to receive the light of the fourth partial wavelength region reflected from the subject, and controls the third light receiving element 253 to receive the light of the fifth partial wavelength region reflected from the subject.

In this way, at a predetermined timing, the control section 105 controls, to be caused from the subject, the light of the first partial wavelength region included in the first wavelength region, the light of the second partial wavelength region included in the second wavelength region, and the light of the fifth partial wavelength region included in the third wavelength region. In addition, at a timing other than the predetermined timing, the control section 105 controls, to be caused from the subject, the light of the third partial wavelength region included in the first wavelength region, the light of the fourth partial wavelength region included in the second wavelength region, and the light of the sixth partial wavelength region included in the third wavelength region.

As explained above, the control section 105 controls the wavelength region of the light to be received by the first light receiving element 251, the second light receiving element 252, and the third light receiving element 253, at respective timings. Then, the image generating section 140 generates an image of a subject, based on the amount of light received by the light receiving element at respective timings, as explained below.

The image generating section 140 generates a first visible light image 620a based on the amount of light received by the light receiving element at the timing represented by the time t600. The image generating section 140 also generates a second visible light image 620b based on the amount of light received by the light receiving element at the timing represented by the time t600 and the amount of light received by the light receiving element at the timing represented by the time t601.

Specifically, the image generating section 140 generates the first visible light image 620a, by the amount of light (SR1) received by the first light receiving element 251 and the amount of light (SB1) received by the second light receiving element 252 at the timing represented by the time t600. In addition, the light emission control section 170 controls the light emission section 410 to emit, towards the subject, the light of the first partial wavelength region that is a longer wavelength region than the third partial wavelength region, at the timing represented by the time t600. In addition, the first light receiving element 251 is able to receive the light of the first wavelength region that is a longer wavelength region than the second wavelength region and the third wavelength region. Accordingly, when the first light receiving element 251 has received the light emitted from the light emission section 410 after being reflected from the object existing within the substance, the first light receiving element 251 is able to receive the light of the longest wavelength region from among the first partial wavelength region, the second partial wavelength region, the third partial wavelength region, the fourth partial wavelength region, the fifth partial wavelength region, and the sixth partial wavelength region.

For this reason, the first light receiving element 251 is able to receive light reflected from an object existing at a position deeper from the surface of the substance. Therefore, the image generating section 140 is able to generate the first visible light image 620a that includes an image of an object (e.g., blood vessel image 626a) existing at a position deeper from the surface of the substance, at least based on the light of the first partial wavelength region received by the first light receiving element 251 at a predetermined timing.

In addition, at the timing represented by the time t600, the light emission control section 170 controls the light emission section 410 to emit, towards the subject, the light of the second partial wavelength region and the light of the fifth partial wavelength region being a shorter wavelength region than the fourth partial wavelength region, at the timing represented by the time t600. In addition, the second light receiving element 252 is able to receive the light of the second wavelength region that is a wavelength region shorter than the first wavelength region and the third wavelength region. Accordingly, when the second light receiving element 252 has received the light emitted from the light emission section 410 after being reflected from the object within the substance, the second light receiving element 252 is able to receive the light of the shortest wavelength region from among the first partial wavelength region, the second partial wavelength region, the third partial wavelength region, the fourth partial wavelength region, the fifth partial wavelength region, and the sixth partial wavelength region.

For this reason, the first light receiving element 251 cannot receive the light reflected from an object existing at a deep position, but is able to receive the light reflected from an object existing at a position shallower from the surface of the substance. Therefore, the image generating section 140 can generate a first visible light image 620a that includes an image of an object existing at a position shallow from the surface of the substance (e.g., blood vessel image 622a and blood vessel image 624a) at least based on the light of the second partial wavelength region received by the second light receiving element 252 at a predetermined timing.

In this way, the image generating section 140 is able to generate the first image that indicates an object positioned at either a position shallower from the surface of the substance or a position deeper from the surface of the substance, at least based on the light of the first partial wavelength region having received by the first light receiving element 251 at a predetermined timing and the light of the second partial wavelength region having received by the second light receiving element 252 at the predetermined timing. Note that in the above-explained example, the first light receiving element 251 has received light of a wavelength region longer than the wavelength regions received by the other light receiving elements, and the second light receiving element 252 has received light of a wavelength region shorter than the wavelength regions received by the other light receiving elements. However, it is needless to say that the second light receiving element 252 may receive light of a wavelength region longer than the wavelength regions received by the other light receiving elements, and the first light receiving element 251 may receive light of a wavelength region shorter than the wavelength regions received by the other light receiving elements.

The image generating section 140 generates a second visible light image 620a by the amount of light (SR2) received by the first light receiving element 251, the amount of light received by the second light receiving element 252 (SB2), the amount of light received by the third light receiving element 253 (SG2), at the timing represented by the time t602, and the aforementioned SR1, SB1, and SG1.

Specifically, the image generating section 140 adds SR1, SR2, SG1, SG2, SB1, and SB2 at a predetermined weight to each pixel, to calculate the amount of light SR for R component for each pixel. Likewise, the image generating section 140 adds R1, SR2, SG1, SG2, SB1, and SB2 at a predetermined weight to each pixel, to calculate the amount of light SG of G component and the amount of light SB of B component for each pixel. Then the image generating section 140 calculates the second visible light image 620b based on the calculated SR, SG, and SB.

Note that the image generating section 140 may also calculate SR, SG, and SB by calculating SR=SR1+SR2, SB=SB1+SB2, and SG=SG1+SG2. In this way, the image generating section 140 may generate the second visible light image based on the summation between the amount of light of the first partial wavelength region received by each first light receiving element 251 at a predetermined timing and the amount of light of the third partial wavelength region received by each first light receiving element 251 at a timing other than the predetermined timing, and based on the summation between the amount of light of the second partial wavelength region received by each second light receiving element 252 at the predetermined timing and the amount of light of the fourth partial wavelength region received by each second light receiving element 252 at a timing other than the predetermined timing.

As explained above, the image generating section 140 generates the second image that indicates the image of the subject, from the light of the first partial wavelength region received by the first light receiving element 251 at the predetermined timing, the light of the third partial wavelength region received by the first light receiving element 251 at a timing other than the predetermined timing, the light of the second partial wavelength region received by the second light receiving element 252 at the predetermined timing, as well as the light of the fourth partial wavelength region received by the second light receiving element 252 at a timing other than the predetermined timing.

In addition, the image generating section 140 may generate a composite image by combining the first visible light image 620a and the second visible light image 620b. In this operation, the image generating section 140 may generate a composite image by overlapping the first visible light image onto the second visible light image with an emphasis on the first visible light image. For example, the image generating section 140 may generate a composite image by overlapping the pixel value emphasized image of the first visible light image 620a onto the second visible light image 620b. The output section 180 may output the first visible light image and the second visible light image generated by the image generating section 140 in association with each other.

As explained above, the image generating section 140 generates the first visible light image by combining at least one of the light of the first partial wavelength region received by the first light receiving element 251 at a predetermined timing, the light of the third partial wavelength region received by the first light receiving element 251 at a timing other than the predetermined timing, the light of the second partial wavelength region received by the second light receiving element 252 at the predetermined timing, the light of the fourth partial wavelength region received by the second light receiving element 252 at a timing other than the predetermined timing, the light of the fifth partial wavelength region received by the third light receiving element 253 at the predetermined timing, and the light of the sixth partial wavelength region received by the third light receiving element 253 at a timing other than the predetermined timing. The image generating section 140 also generates the second visible light image by a combination different from the combination selected for the first visible light image.

The image capturing system 10 of the present embodiment is able to provide a first visible light image in which the blood vessels both on the surface as well as deeper from the surface are emphasized, and a second visible light image 620b for surface observation. For this reason, when the image capturing system 10 is actually applied, for example when a doctor performs operation or the like while observing the image displayed on the output section 180, he or she has a chance of recognizing the blood vessels existing deep inside that are difficult to locate from surface observation. In addition, it is an advantage to allow a doctor to perform operation or the like by referring to the image in which the blood vessels are emphasized.

In addition, the image capturing system 10 is able to receive light from a plurality of partial wavelength regions for each of the wavelength regions received by the light receiving elements, thereby enabling to calculate the reflectivity of the light from the subject for each partial wavelength region. For example, the image capturing system 10 is able to calculate the reflectivity of the light from the subject for each partial wavelength region based on the amount of emitted light and the amount of received light for each of the partial wavelength regions indicated by B1, B2, G1, G2, R2, and R1 shown in FIG. 3.

In addition, the image capturing system 10 is able to calculate the reflectivity of each partial wavelength region for each pixel. In addition, the image capturing system 10 can identify a position of an abnormal portion of a gastrocolic membrana mucosa, by comparing the spectral reflectivity of the membrane mucosa such as shown by the line 340 in FIG. 3 to the reflectivity for each pixel.

In addition, the image capturing system 10 calculates the absorption ratio of each partial wavelength region from the reflectivity of each partial wavelength region. Also based on the absorption ratio, the image capturing system 10 may be able to calculate a component included in the analyte 20 based on the absorption ratio. For example, the image capturing system 10 can sometimes calculate the ratio of the components in the blood, by irradiating light of wavelength regions different in absorption ratio in various components in the blood such as oxygenated hemoglobin and reduced hemoglobin, from the light irradiation section 150, thereby enabling to calculate the oxygen concentration in the blood or the like.

In addition, the control section 105 may control the light irradiation section 150 to irradiate the light of a partial wavelength region of a narrow bandwidth that has a characteristic reflectivity in the spectral reflectivity for a particular type of subject. The image capturing system 10 according to the present embodiment is able to control the wavelength region of the light received by the light receiving element that has a unique spectral sensitivity characteristic, by controlling the wavelength region irradiated by the light irradiation section 150, thereby enabling to reduce the size of the endoscope 100.

Figure 7:
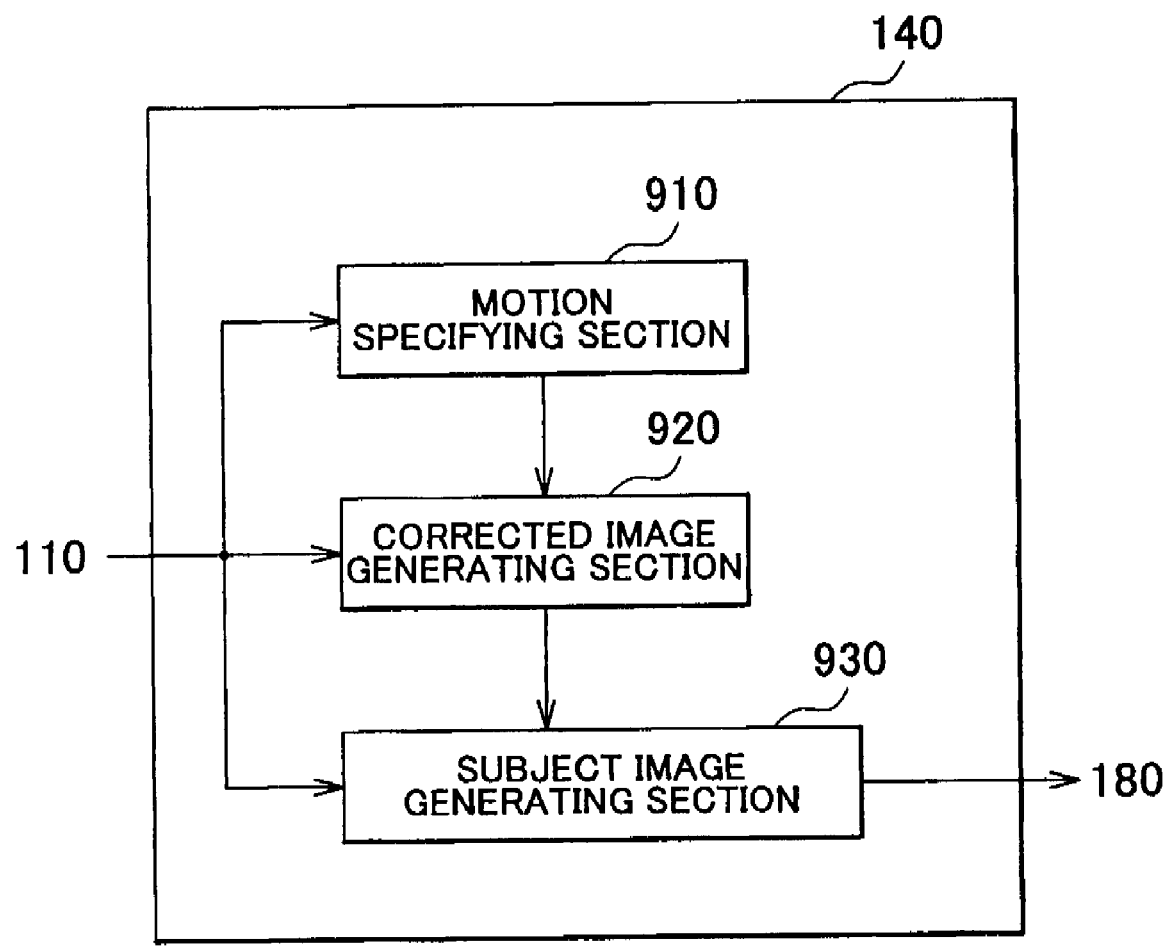
FIG. 7 shows an exemplary block configuration of the image generating section 140.

FIG. 7 shows an exemplary block configuration of the image generating section 140. FIG. 6 deals with a case of combining the first visible light image 620a and the first visible light image 620b, assuming that there is substantially no factor that causes the temporal change in image, such as a motion of the tip 102 of the endoscope 100 or the motion of the analyte 20 for the purpose of facilitating explanation. In this combining operation, it is possible that the object position be different between the first visible light image 620a and the first visible light image 620b, when there actually is a motion of the tip 102 of the endoscope 100 or the motion of the analyte 20.

The present drawing shows the operation and the function of the image generating section 140 for correcting the effect of the aforementioned motions to the visible light image, as well as the configuration of the image generating section 140. The image generating section 140 includes a motion specifying section 910, a corrected image generating section 920, and a subject image generating section 930.

Based on visible light images at a plurality of timings, the motion specifying section 910 specifies the motion of the object in the images. Here, the motion of the object includes a motion of the analyte 20 itself, a motion of the tip 102 of the endoscope 100, the temporal change of the zoon value of the image capturing section 110, and the motion that causes the temporal change of the image. In addition, the motion of the tip 102 of the endoscope 100 includes a temporal change in position of the tip 102 that causes the temporal change of an image capturing position of the image capturing section 110 and the temporal change in direction of the tip 102 that causes the temporal change of the image capturing direction of the image capturing section 110.

Here, the motion specifying section 910 specifies the motion of the object based on the visible light images at the time t600 and the time t601. For example, the motion specifying section 910 may specify the motion of an object, by matching each extracted object from a plurality of visible light images.

The corrected image generating section 920 corrects an image signal representing the visible light image at the time t601, based on the motion, thereby generating an image signal representing the visible light image to be obtained at the time t602. Accordingly, the corrected image generating section 920 can generate the image of the subject at the time t602.

Figure 8:
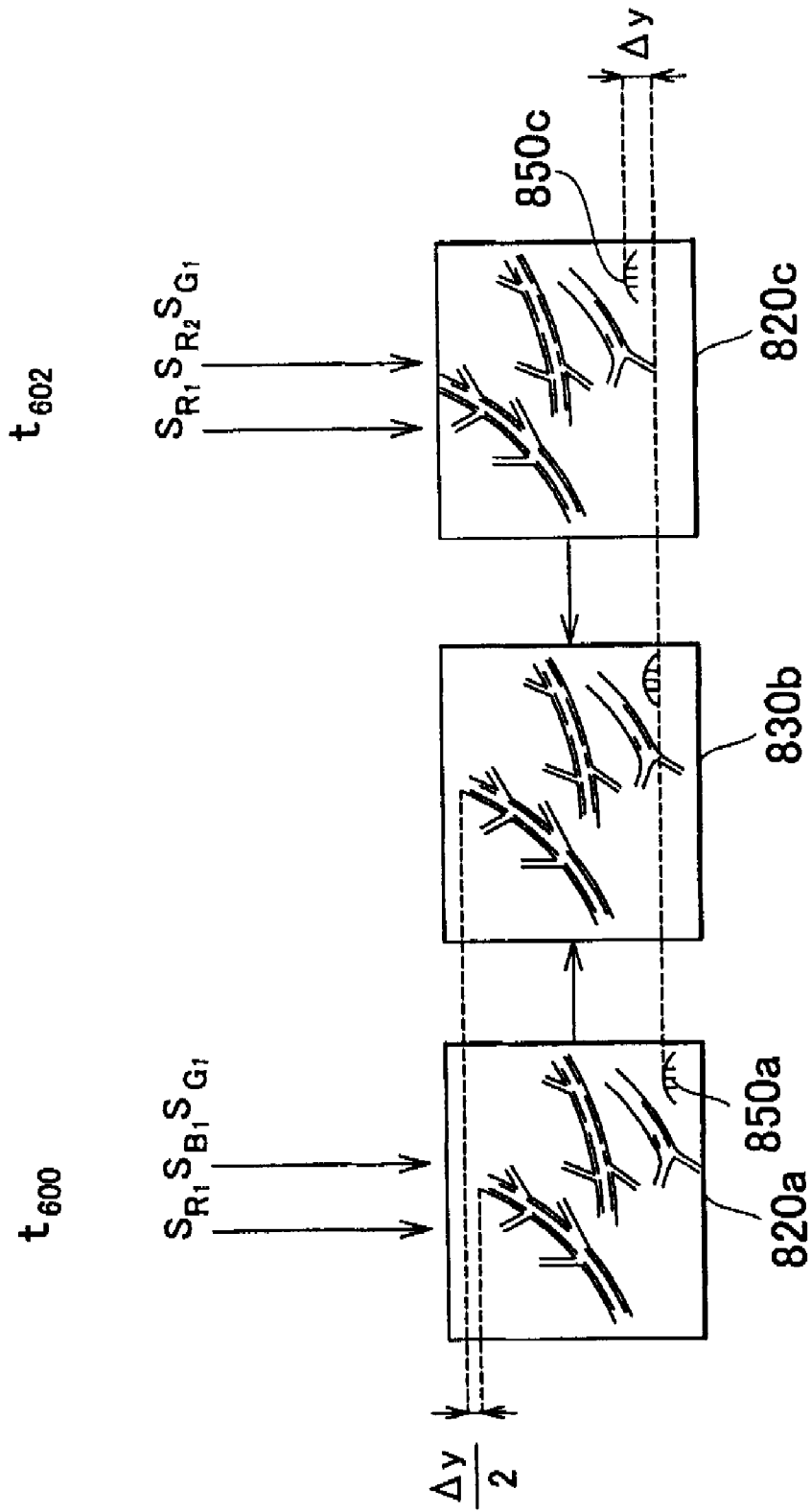
FIG. 8 explains generation of a visible light image in which the motion is corrected.

FIG. 8 explains generation of a visible light image in which the motion is corrected. The visible light image 820a is generated from a image signal from the first light receiving element 251 and the second light receiving element 252 at the time t600. In addition, the visible light image 820c is generated from an image signal from the first light receiving element 251 and the second light receiving element 252 at the time t602.

Here, the motion specifying section 910 specifies the motion based on the image contents of the visible light image 820a and the visible light image 820c. Specifically, the motion specifying section 910 extracts objects representing the same subject, from the visible light image 820a and the visible light image 820c. In the present example, the motion specifying section 910 extracts the object 850a and the object 850c, from the visible light image 820a and the visible light image 820c, respectively.

The motion specifying section 910 calculates the difference in respective positions of the object 850a and the object 850c. In the example of the drawing, the motion specifying section 910 calculates the positional difference Δy between the object 850a and the object 850c, assuming that there is a positional difference in y direction higher in the image to simplify the explanation. The corrected image generating section 920 generates the visible light image 830b by shifting the image 821a in the direction y, by the amount of Δy/2 in accordance with the calculated positional difference Δy and each timing of the time t600, the time t601, and the time t602.

The aforementioned explanation is about specifying the motion using the visible light image 820. However, the image of each color component may also be used to specify the motion. Here, the motion specifying section 910 may use the contrast of the captured image to decide which image of wavelength to be used for specifying the motion by the motion specifying section 910. For example, the motion specifying section 910 may prioritize an image having a larger contrast when specifying the motion. When an image having a microstructure can be used as an object for motion specification such as when the image of the microstructure of the surface is clear for example, the motion can be more accurately specified using the image of B signal (e.g., $S_{B1}$ image). In addition, when an image of a concave/convex structure is used as an object for motion specification such as when the image of the concave/convex structure on the surface is clear, the motion can be more accurately specified using the image of G signal (e.g., $S_{G1}$ image).

The corrected image generating section 920 may apply a different amount of correction of motion for each image region in a visible light image. For example, when the image capturing direction of the image capturing section 110 is vertical to the surface of a subject, and the tip 102 of the endoscope 100 moves horizontally with respect to the surface of the subject, the amount of motion of the object can be considered to be equal to each image region. However, for example when the image capturing direction of the image capturing section 110 is not vertical to the surface of the subject, the amount of motion in an image region in which a region far from the tip 102 is captured will have a small amount of motion than in an image region in which a region close to the tip 102 is captured.

So that the corrected image generating section 920 calculates the amount of correction of motion with respect to a visible light image for each image region, the positional relation between the surface of a subject and the image capturing section 110 should be known or should be estimated, by which the amount of correction of motion can be calculated based on the positional relation and the position of the image region. Note that the corrected image generating section 920 may acquire a control value for operating the endoscope 100 for causing a temporal change in image, such as a control value for controlling the position or the direction of the tip 102 and a control value for controlling a zoom value of the image capturing section 110, so as to calculate the amount of correction of motion with respect to the visible light image based on the control value.

The motion specifying section 910 may alternatively calculate the motion of an object for each image region. The corrected image generating section 920 may calculate the amount of correction of motion with respect to the image in each image region based on the motion of the object for each image region.

Note that when specifying the motion for each image region, the motion specifying section 910 may decide which image of wavelength to be used in specifying the motion for each image region. The motion specifying section 910 calculates the contrast for each image for each image region, for example. Then the motion specifying section 910 may select images of different wavelengths of which a larger contrast is calculated over the other images for respective image regions, to use the selected images in specifying the motion of the object.

Note that in the above example, the visible light image 820a and the visible light image 820c are used to specify the motion. However, the motion specifying section 910 may use the visible light image 820a and the visible light image generated by the light of the same wavelength region obtained prior to the time t600.

When the display of a visible light image can be delayed to some extent, the motion specifying section 910 may specify the motion from images obtained at a plurality of timings including a timing around the time t601 that is a targeted time at which the visible light image in which the motion is corrected is to be generated. The accuracy in specifying the motion can sometimes be enhanced by utilizing images of later timings. Note that the motion specifying section 910 may specify the motion by using visible light images (or images of each color component) captured at three or more timings.

The subject image generating section 930 may generate a second visible light image which is an example of a subject image of the present invention, by combining the visible light image 830b and the visible light image captured at the time t601. Accordingly, the second visible light image in which the motion is corrected can be obtained by utilizing visible light images captured at different timings.

The aforementioned example deals with the operation of the image generating section 140 when correcting the motion for generating the second visible light image at the time t601. The corrected image generating section 920 may also generate a first visible light image in which the motion is corrected based on the motion specified by the motion specifying section 910. The subject image generating section 930 may output, to the output section 180, a combined image of the first visible light image in which the motion is corrected and the second visible light image in which the motion is corrected.

In addition, the aforementioned example deals with the generation of various visible light images at the time t601. However, the similar processing can be used to generate various visible light images at the time t602. For example, the motion specifying section 910 may use the visible light images (or images of respective color components) obtained at the time t601 and the time t603 respectively in specifying the motion. The corrected image generating section 920 may correct various visible light images obtained at the time t601, according to the motion.

As explained above in connection with FIGS. 7 and 8, the motion specifying section 910 specifies the motion of an object on an image among a plurality of timings, based on the light of the first partial wavelength region received by the first light receiving element 251 at a plurality of timings including the predetermined timing, as well as the light of the second partial wavelength region received by the second light receiving element 252 at the plurality of timings. The corrected image generating section 920 generates a corrected image which is an image of a subject generated by the light of the first partial wavelength region and the light of the second partial wavelength region at a timing other than the predetermined timing, based on the light of the first wavelength region received by the first light receiving element 251 at the predetermined timing and the light of the second wavelength region received by the second light receiving element 252 at the first timing. The subject image generating section 930 may generate a second image based on the corrected image and an image generated by the light of the third partial wavelength region received by a plurality of first light receiving elements at a timing other than the predetermined timing, and the light of the fourth partial wavelength region received by a plurality of second light receiving elements at a timing other than the predetermined timing.

Figure 9:
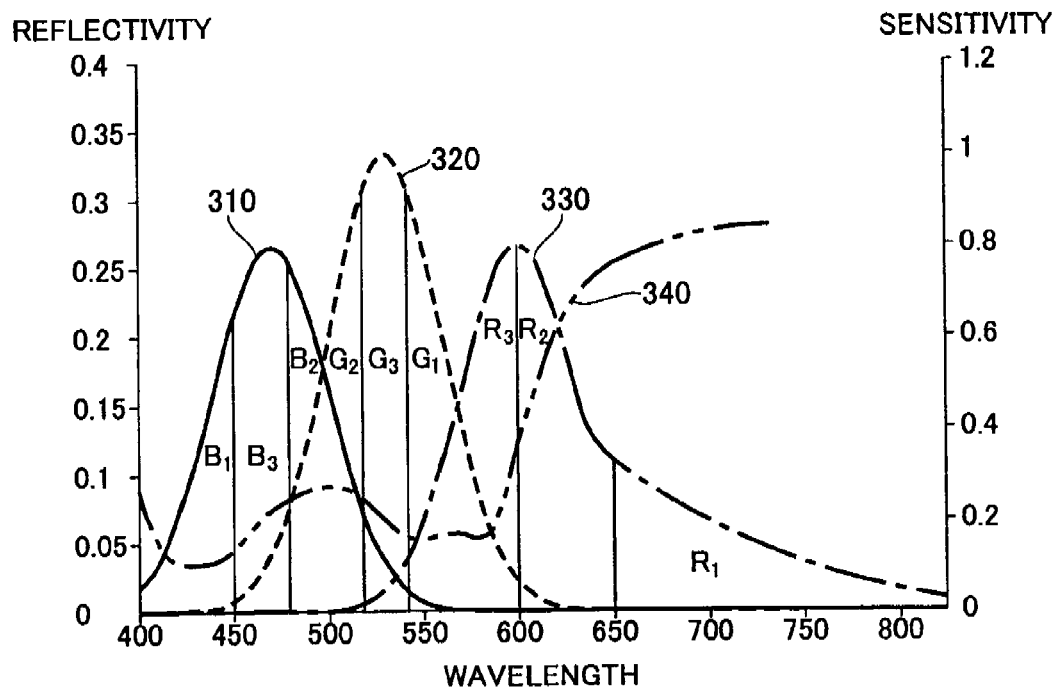
FIG. 9 shows an example of a spectral sensitivity characteristic of a light receiving element and a configuration of the light source filter 420.
Figure 9:
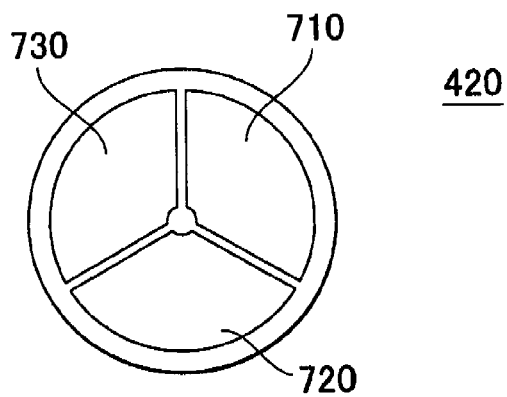

FIG. 9 shows an example of a spectral sensitivity characteristic of a light receiving element and a configuration of the light source filter 420. The following explanation focuses on the differences from the spectral sensitivity characteristic and the function of the light source filter 420 in FIGS. 4 and 5. The present drawing shows a spectral sensitivity characteristic in a wavelength region including a wavelength region longer than the wavelength region shown in FIG. 3. As shown in this drawing, the first light receiving element 251 can receive light in an infrared region (e.g., 810 nm) which is one example of the specific wavelength region.

In the present drawing, the light source filter 420 includes irradiation light filters 710, 720, and 730. The irradiation light filter 710 cuts off light of the third partial wavelength region (R2), light of the fourth partial wavelength region (B2), light of the sixth partial wavelength region (G2), light of the seventh partial wavelength region (R3), light of the eighth partial wavelength region (B3), and light of ninth partial wavelength region (G3), and transmits excitation light, light of the second partial wavelength region (B1), and light of the fifth partial wavelength region (G1). In addition, the irradiation light filter 720 cuts off excitation light, light of the second partial wavelength region (B1), light of the fifth partial wavelength region (G1), light of the seventh partial wavelength region (R3), light of the eighth partial wavelength region (B3), and light of the ninth partial wavelength region (G3), and transmits light of the third partial wavelength region (R2), light of the fourth partial wavelength region (B2), and light of the sixth partial wavelength region (G2). In addition, the irradiation light filter 730 cuts off excitation light, light of the second partial wavelength region (B1), light of the third partial wavelength region (R2), light of the fourth partial wavelength region (B2), and light of the fifth partial wavelength region (G1), and light of the sixth partial wavelength region (G2), and transmits light of the seventh partial wavelength region (R3), light of the eighth partial wavelength region (B3), and light of the ninth partial wavelength region (G3).

Therefore, at the timing at which the light from the light emission section 410 is guided toward the irradiation light filter 730, from among the light from the light emission section 410, the excitation light, the light of the second partial wavelength region, and the light of the fifth partial wavelength region are transmitted through the irradiation light filter 710 to irradiate the subject. At the timing at which the light from the light emission section 410 is guided towards the irradiation light filter 720, from among the light from the light emission section 410, the light of the third partial wavelength region, the light of the fourth partial wavelength region, and the light of the sixth partial wavelength region are transmitted through the irradiation light filter 720 to irradiate the subject. At the timing at which the light from the light emission section 410 is guided towards the irradiation light filter 730, from among the light from the light emission section 410, the light of the seventh partial wavelength region (R3), the light of the eighth partial wavelength region (B3), and the light of the ninth partial wavelength region (G3) are transmitted through the irradiation light filter 730 to irradiate the subject.

FIG. 10 shows an example of an image capturing timing of the image capturing section 110 and an image generated by an image generating section 140. The image capturing control section 160 controls the image capturing section 110 to perform image capturing at the time t800, the time t801, the time t802, the time t803, . . . . By the timing control by the image capturing control section 160, the light emission control section 170 irradiates the light emitted from the light emission section 410 onto the subject via the irradiation light filter 710, at the first timing including the time t800 and the time t803. According to this arrangement, the excitation light, the light of the second partial wavelength region, and the light of the fifth partial wavelength region irradiate the subject.

The image generating section 140 generates a luminescence light image 820a at the time t800, based on the amount of luminescence light received by the first light receiving element 251. Since the excitation light reaches deeper in a substance than the light of the other partial wavelength regions, the luminescence light image 820a contains the blood vessel images 822a and 824a at shallow positions from the surface of the substance, as well as the blood vessel image 826a at a deep position.

The light emission control section 170 irradiates the light emitted from the light emission section 410 via the irradiation light filter 720, at the time t801, by the timing control by the image capturing control section 160. Accordingly, the light of the third partial wavelength region, the light of the fourth partial wavelength region, and the light of the sixth partial wavelength region irradiate the subject.

By the timing control by the image capturing control section 160, the light emission control section 170 irradiates the subject with the light emitted from the light emission section 410 via the irradiation light filter 730 at the time t802. Accordingly, the light of the seventh partial wavelength region (R3), the light of the eighth partial wavelength region (B3), the light of the ninth partial wavelength region (G3) irradiate the subject. The image generating section 140 generates the first visible light image 820b based on the amount of light (SB1) received by the second light receiving element 252 at the time t800 and the amount of light (SR2) received by the first light receiving element 251 at the time t801. Just as the first visible light image 620b, the first visible light image 820b contains the image of an object existing at a deeper position from the surface of the substance (e.g., the blood vessel image 826b) and the image of an object existing at a shallow position from the surface of the substance (e.g., the blood vessel image 822b and the blood vessel image 624b).

At the timing represented by the time t800, the image generating section 140 generates the second visible light image 820c based on the amount of light received by the light receiving elements other than the first light receiving element 251 at the timing represented by the time t800 (SB1 and SG1), the amount of light received by each light receiving element at the timing represented by the time t801 (SB2, SG2, and SR2), and the amount of light received by each light receiving element at the timing represented by the time t803 (SB3, SG3, and SR3). Note that the image generating section 140 can generate the second visible light image 820c just as in the method explained with reference to FIG. 6.

For example, the image generating section 140 is able to generate the second visible light image 820c, by summing the SB1, SG1, SB2, SG2, SR2, SB3, SG3, and SR3 by adding thereto a predetermined weight thereby obtaining the SR, SG, and SB. The second visible light image 820c contains an image of an object existing at a relatively shallow position (e.g., blood vessel images 822c and 824c).

In this way, according to the image capturing system 10 of the present embodiment, the luminescence light image 820a can be obtained by the luminescence light of an infrared region caused from the analyte 20 by means of the excitation light of the infrared region. The excitation light having a longer wavelength than the visible light is hard to be absorbed by a substance than the visible light. Therefore, the excitation light enters deeper in the substance than the visible light, to cause the analyte 20 to generate luminescence light. In addition, the luminescence light has a wavelength even longer than the wavelength of the excitation light, and so is easy to reach the surface of the substance. Therefore, the image capturing system 10 can obtain the blood vessel image of a depth range wider than the visible light at once.

In the embodiments explained in connection with FIGS. 9 and 10, the corrected image generating section 920 is able to generate a first visible light image in which the motion is corrected and a luminescence light image, using the similar processing as the processing described in connection with FIGS. 7 and 8. The subject image generating section 930 may generate a second visible light image by combining visible light images in which the motion is corrected, or an image in which the second visible light image is combined with a luminescence light image.

So far, the embodiments of the present invention have been explained in a case where the control section 105 causes light of a different wavelength region from a subject at a different timing. So as to obtain an image of light of a different wavelength region, the main wavelength component in a light spectrum from a subject should be in a predetermined wavelength region, and a certain spectral intensity can remain in the other wavelength regions. For example, the light from a subject at a predetermined timing may have a spectral intensity in the third partial wavelength region and in the fourth partial wavelength region, in addition to the first partial wavelength region and the second partial wavelength region. If light from a subject at a predetermined timing has a spectral intensity mainly in the first partial wavelength region and in the second partial wavelength region, the image of the first partial wavelength region and the second partial wavelength region can be substantially generated.

In this way, the control section 105 may cause light of a different spectrum from a subject at a different timing, in each of the first wavelength region and the second wavelength region. For example, the control section 105 may control the light irradiation section 150 to irradiate light that causes the ratio of the spectral intensity of the third partial wavelength region with respect to the spectral intensity of the first partial wavelength region in the light from the subject to be larger at a timing other than a predetermined timing than at the predetermined timing. More specifically, the control section 105 may cause the light irradiation section 150 to irradiate light that causes the spectral intensity of the first partial wavelength region to be larger than the spectral intensity of the third partial wavelength region at a predetermined timing, and to irradiate light that causes the spectral intensity of the third partial wavelength region to be larger than the spectral intensity of the first partial wavelength region at a timing other than the predetermined timing.

Likewise, the control section 105 may control the light irradiation section 150 to irradiate light that causes the ratio of the spectral intensity of the fourth partial wavelength region with respect to the spectral intensity of the second partial wavelength region in the subject light to be larger at a timing other than the predetermined timing than at the predetermined timing. More specifically, the control section 105 may cause the light irradiation section 150 to irradiate light that causes the spectral intensity of the second partial wavelength region to be larger than the fourth partial wavelength region at the predetermined timing, and to irradiate light that causes the spectral intensity of the fourth partial wavelength region to be larger than the spectral intensity of the second partial wavelength region at a timing other than the predetermined timing.

The image generating section 140 may generate a first image by a combination of light of a first spectrum from a subject received by the first light receiving element 251 at the predetermined timing, light of a second spectrum from the subject received by the second light receiving element 252 at the predetermined timing, light of a third spectrum from the subject received by the first light receiving element 251 at a timing other than the predetermined timing, and light of a fourth spectrum from the subject received by the second light receiving element 252 at a timing other than the predetermined timing. The image generating section 140 may also generate a second image by a combination different from the aforementioned combination to generate the first image.

In connection with FIGS. 4, 5, and 9, described is the operation to temporarily control the spectrum of the irradiation light emitted from the light emission section 410 by rotating the light source filter 420 as an operation of the light irradiation section 150. As another example of the light irradiation section 150, the light irradiation section 150 does not have to include a light source filter 420. Specifically, the light emission section 410 may include a plurality of light emitting elements emitting a different spectrum of light from each other. The control section 105 may control light emission at the predetermined timing and at a timing different from the predetermined timing.

For example, the light emission section 410 may include a light emitting element that emits light of a red wavelength region, a light emitting element that emits a blue wavelength region, a light emitting element that emits light of a green wavelength region, and a light emitting element that emits light of an excitation light wavelength region. An example of light emitting element that emits light of a visible light region is a semiconductor device such as LED. An example of light emitting element that emits excitation light is a semiconductor device such as a semiconductor laser. In addition, the light emitting element may be a phosphor that emits luminescence light such as fluorescence by being excited.

The control section 105 can control the spectrum of light to irradiate the subject, by controlling the light emission intensity of each of the plurality of light emitting elements at each timing. Note that "to control the light emission intensity of each of the plurality of light emitting elements" includes control to have a different combination of light emitting elements that emit light at each timing. In addition, a light emitting element may include a filter for selectively transmitting light of the specific wavelength region and a light emitter. If this light emitter emits light and the spectrum of light after being transmitted through a filter is different for each filter, the light emitting elements can be considered as a plurality of light emitting elements that respectively emit light of a different spectrum from each other in the present invention.

Note that a light emitting element can be provided for the tip 102 of the endoscope 100. Note that the light emitting element may emit light by means of electric excitation, or may emit light by optical excitation. When the light emitting element emits light by optical excitation, the light irradiation section 150 includes an excitation section that emits light for exciting the light emitting element, and the light emitting element. Here, the light emitting element may emit light of a different spectrum for a different wavelength of light for excitation. In this case, the control section 105 may control the spectrum of irradiation light by controlling the wavelength of light for excitation emitted from the light emitting section at each timing. The spectrum of light emitted by each light emitting element by means of the light for excitation may be different for each light emitting element. In addition, from among the light for excitation, the light transmitted through the light emitting element may be irradiated onto the subject as irradiation light.

Figure 11:
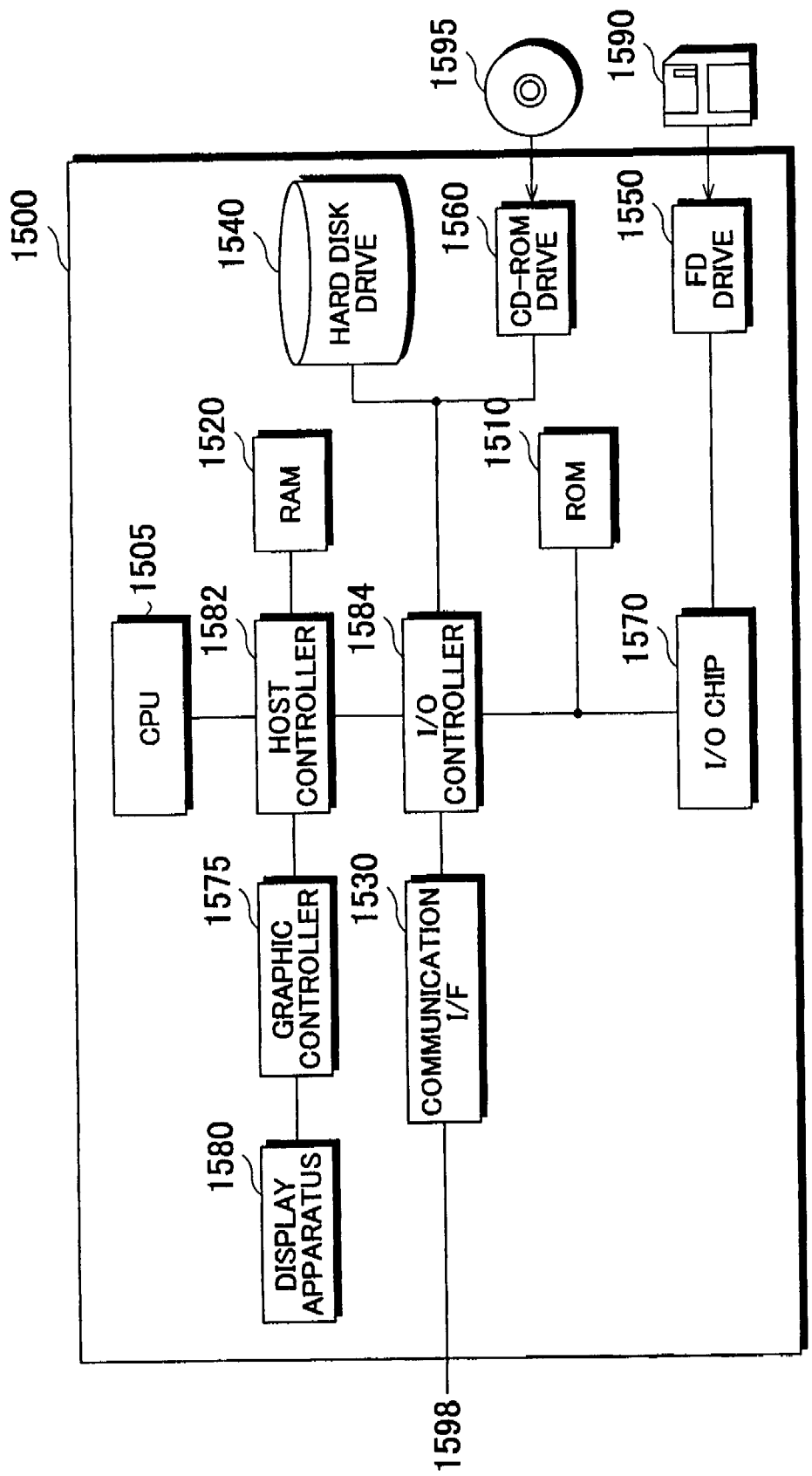
FIG. 11 shows an exemplary hardware configuration of a computer 1500 that functions as an image capturing system 10.

FIG. 11 shows an exemplary hardware configuration of a computer 1500 that functions as an image capturing system 10. The image capturing system 10 according to the present embodiment is provided with a CPU peripheral section, an input/output section, and a legacy input/output section. The CPU peripheral section includes a CPU 1505, a RAM 1520, a graphic controller 1575, and a display apparatus 1580 connected to each other by a host controller 1582. The input/output section includes a communication interface 1530, a hard disk drive 1540, and a CD-ROM drive 1560, all of which are connected to the host controller 1582 by an input/output controller 1584. The legacy input/output section includes a ROM 1510, a flexible disk drive 1550, and an input/output chip 1570, all of which are connected to the input/output controller 1584.

The host controller 1582 is connected to the RAM 1520 and is also connected to the CPU 1505 and the graphic controller 1575 accessing the RAM 1520 at a high transfer rate. The CPU 1505 operates to control each section based on programs stored in the ROM 1510 and the RAM 1520. The graphic controller 1575 obtains image data generated by the CPU 1505 or the like on a frame buffer provided inside the RAM 1520 and displays the image data in the display apparatus 1580. Alternatively, the graphic controller 1575 may internally include the frame buffer storing the image data generated by the CPU 1505 or the like.

The input/output controller 1584 connects the communication interface 1530 serving as a relatively high speed input/output apparatus, the hard disk drive 1540, and the CD-ROM drive 1560 to the host controller 1582. The communication interface 1530 communicates with other apparatuses via a network. The hard disk drive 1540 stores the programs and data used by the CPU 1505 in the image capturing system 10. The CD-ROM drive 1560 reads the programs and data from a CD-ROM 1595 and provides the read programs and data to the hard disk drive 1540 via the RAM 1520.

Furthermore, the input/output controller 1584 is connected to the ROM 1510, and is also connected to the flexible disk drive 1550 and the input/output chip 1570 serving as a relatively low speed input/output apparatus. The ROM 1510 stores a boot program executed when the image capturing system 10 starts up, a program relying on the hardware of the image capturing system 10, and the like. The flexible disk drive 1550 reads programs or data from a flexible disk 1590 and supplies the read programs or data to the hard disk drive 1540 via the RAM 1520. The input/output chip 1570 is connected to a variety of input/output apparatuses via the flexible disk drive 1550, and a parallel port, a serial port, a keyboard port, a mouse port, or the like, for example.

A communication program supplied to the hard disk drive 1540 via the RAM 1520 is provided by a user in a state where it is stored in a storage medium, such as the flexible disk 1590, the CD-ROM 1595, or an IC card. The communication program is read from the recording medium, installed via the RAM 1520 to the hard disk drive 1540 in the image capturing system 10, and is executed by the CPU 1505. The communication program installed to the image capturing system 10 to be executed acts on the CPU 1505 to cause the image capturing system 10 to function as the image capturing section 110, the image generating section 140, the output section 180, the control section 105, and the light irradiation section 150 explained with reference FIGS. 1-10.

Although some aspects of the present invention have been described by way of exemplary embodiments, it should be understood that those skilled in the art might make many changes and substitutions without departing from the spirit and the scope of the present invention which is defined only by the appended claims.

What is claimed is:

1. An image capturing system comprising:
an image capturing section that includes a plurality of first light receiving elements for receiving light of a first wavelength region and a plurality of second light receiving elements for receiving light of a second wavelength region;

a control section that causes to be generated, from a subject, light of a different spectrum at a different timing for each of the first wavelength region and the second wavelength region; and an image generating section that generates a first image from a combination that includes at least one of light of a first spectrum from the subject received by the plurality of first light receiving elements at a predetermined timing, light of a second spectrum from the subject received by the plurality of second light receiving elements at the predetermined timing, light of a third spectrum from the subject received by the plurality of first light receiving elements at a timing other than the predetermined timing, and light of a fourth spectrum from the subject received by the plurality of second light receiving elements at the timing other than the predetermined timing, and generates a second image from a combination different from the combination used to generate the first image;

wherein the control section causes to be generated, from the subject, light of a first partial wavelength region included in the first wavelength region and light of a second partial wavelength region included in the second wavelength region at the predetermined timing, and causes to be generated, from the subject, light of a third partial wavelength region included in the first wavelength region and light of a fourth partial wavelength region included in the second wavelength region at the timing other than the predetermined timing, and the image generating section generates the first image from a combination that includes at least one of light of the first partial wavelength region from the subject received by the plurality of first light receiving elements at the predetermined timing, the light of the third partial wavelength region from the subject received by the plurality of first light receiving elements at the timing other than the predetermined timing, the light of the second partial wavelength region from the subject received by the plurality of second light receiving elements at the predetermined timing, and the light of the fourth partial wavelength region from the subject received by the plurality of second light receiving elements at the timing other than the predetermined timing;

and further comprising:

a light emission section that causes to be emitted, from the subject, light of the first partial wavelength region, the second partial wavelength region, the third partial wavelength region, and the fourth partial wavelength region, wherein the control section controls the light emission section to emit the light which causes the light of the first partial wavelength region and the light of the second partial wavelength region emitting from the subject at the predetermined timing, and controls the light emission section to emit the light of the third partial wavelength region and the light of the fourth partial wavelength region from the subject at the timing other than the predetermined timing;

wherein the plurality of first light receiving elements and the plurality of second light receiving elements receive the light emitted by the light emission section after being reflected from an object existing inside a substance, the first wavelength region that is shorter than the second wavelength region, and the image generating section generates the first image based at least on the light of the first partial wavelength region received by the plurality of first light receiving elements at the predetermined timing; and wherein the first partial wavelength region is shorter than the third partial wavelength region and the second partial wavelength region is longer than the fourth partial wavelength region, at the predetermined timing, and the first image represents an image of an object existing at a shallower position from the surface of the substance and an object existing at a deeper position from the surface of the substance, and the image generating section generates the first image based at least on the light of the first partial wavelength region received by the plurality of first light receiving elements at the predetermined timing and the light of the second partial wavelength region received by the plurality of second light receiving elements at the predetermined timing.

2. The image capturing system according to claim 1, wherein the light emission section emits the light of the first partial wavelength region, the second partial wavelength region, the third partial wavelength region, and the fourth partial wavelength region, the control section controls the light emission section to emit the light of the first partial wavelength region and the light of the second partial wavelength region towards the subject at the predetermined timing, and controls the light emission section to emit the light of the third partial wavelength region and the light of the fourth partial wavelength region towards the subject at the timing other than the predetermined timing, at the predetermined timing, the plurality of first light receiving elements receive the light of the first partial wavelength region reflected from the subject, and the plurality of second light receiving elements receive the light of the second partial wavelength region reflected from the subject, and at the timing other than the predetermined timing, the plurality of first light receiving elements receive the light of the third partial wavelength region reflected from the subject, and the plurality of second light receiving elements receive the light of the fourth partial wavelength region reflected from the subject.

3. The image capturing system according to claim 2, wherein the image capturing section further includes a plurality of third light receiving elements for receiving light of a third wavelength region, the light emission section emits light of a fifth partial wavelength region and a sixth partial wavelength region included in the third wavelength region, the control section controls the light emission section to emit the light of the first partial wavelength region, the light of the second partial wavelength region, and the light of the fifth partial wavelength region towards the subject at the predetermined timing, and to emit the light of the third partial wavelength region, the light of the fourth partial wavelength region, and the light of the sixth partial wavelength region towards the subject at the timing other than the predetermined timing, at the predetermined timing, the plurality of first light receiving elements receive the light of the first partial wavelength region reflected from the subject, the plurality of second light receiving elements receive the light of the second partial wavelength region reflected from the subject, and the plurality of third light receiving elements receive the light of the fifth partial wavelength region reflected from the subject, and at the timing other than the predetermined timing, the plurality of first light receiving elements receive the light of the third partial wavelength region reflected from the subject, the plurality of second light receiving elements receive the light of the fourth partial wavelength region reflected from the subject, and the third light receiving elements receive the light of the sixth partial wavelength region reflected from the subject, and the image generating section generates a first image from a combination that includes at least one of the light of the first partial wavelength region received by the plurality of first light receiving elements at the predetermined timing, the light of the third partial wavelength region received by the plurality of first light receiving elements at the timing other than the predetermined timing, the light of the second partial wavelength region received by the plurality of second light receiving elements at the predetermined timing, the light of the fourth partial wavelength region received by the plurality of second light receiving elements at the timing other than the predetermined timing, the light of the fifth partial wavelength region received by the plurality of third light receiving elements at the predetermined timing, and the light of the sixth partial wavelength region received by the plurality of third light receiving elements at the timing other than the predetermined timing, and generates a second image from a combination different from the combination used to generate the first image.

4. The image capturing system according to claim 3, wherein the first wavelength region is a blue wavelength region, the second wavelength region is a red wavelength region, and the third wavelength region is a green wavelength region.

5. The image capturing system according to claim 1, wherein the image generating section generates a composite image by combining the first image and the second image.

6. The image capturing system according to claim 5, wherein the image generating section generates the second image, from the light of the first partial wavelength region received by the plurality of first light receiving elements at the predetermined timing, the light of the third partial wavelength region received by the plurality of first light receiving elements at the timing other than the predetermined timing, the light of the second partial wavelength region received by the plurality of second light receiving elements at the predetermined timing, and the light of the fourth partial wavelength region received by the plurality of second light receiving elements at the timing other than the predetermined timing.

7. The image capturing system according to claim 6, wherein the image generating section generates the composite image by overlapping the first image onto the second image with an emphasis on the first image.

8. The image capturing system according to claim 6, further comprising:

an output section that outputs the first image and the second image generated by the image generating section, in association with each other.

9. The image capturing system according to claim 6, wherein the image generating section generates the second image based on a) a summation, for each first light receiving element, of an amount of light of the first partial wavelength region received by the plurality of first light receiving elements at the predetermined timing and an amount of light of the third partial wavelength region received by the plurality of first light receiving elements at the timing other than the predetermined timing, and b) a summation, for each second light receiving element, of an amount of light of the second partial wavelength region received by the plurality of second light receiving elements at the predetermined timing and an amount of light of the fourth partial wavelength region received by the plurality of second light receiving elements at the timing other than the predetermined timing.

10. The image capturing system according to claim 1, further comprising:

a first spectral filter that transmits the light of the first partial wavelength region and the light of the third partial wavelength region; and a second spectral filter that transmits the light of the second partial wavelength region and the light of the fourth partial wavelength region, wherein the plurality of first light receiving elements receive light from the subject after being transmitted through the first spectral filter, and the plurality of second light receiving elements receive light from the subject after being transmitted through the second spectral filter.

11. The image capturing system according to claim 1, wherein the light emission section includes a plurality of light emitting elements that respectively emit light of a different spectrum from each other, and the control section controls the light emission at the predetermined timing and at the timing other than the predetermined timing by controlling respective light emission intensities of the plurality of light emitting elements.

12. The image capturing system according to claim 1, further comprising:

an irradiation light filter that transmits the light of the first partial wavelength region and the light of the second partial wavelength region, wherein the light emission section emits light of a wavelength region, the wavelength region including the first partial wavelength region, the second partial wavelength region, and at least one of the third partial wavelength region and the fourth partial wavelength region, and the control section controls the light from the light emission section to irradiate the subject after being transmitted through the irradiation light filter, at the predetermined timing.

13. The image capturing system according to claim 1, wherein the image generating section includes:

a motion specifying section that specifies a motion of an object in an image at a plurality of timings including the predetermined timing, based on a plurality of images generated by a) the light of the first partial wavelength region received by the plurality of first light receiving elements at the plurality of timings and b) the light of the second partial wavelength region received by the plurality of second light receiving elements at the plurality of timings, and a corrected image generating section that generates a corrected image which is an image of a subject generated by the light of the first partial wavelength region and the light of the second partial wavelength region at the timing other than the predetermined timing, based on the light of the first wavelength region received by the plurality of first light receiving elements at the predetermined timing and the light of the second wavelength region received by the plurality of second light receiving elements at the predetermined timing.

14. The image capturing system according to claim 13, wherein
the image generating section further includes:
a subject image generating section that generates the second image based on the corrected image and on an image generated by the light of the third partial wavelength region received by the plurality of first light receiving elements at the timing other than the predetermined timing and the light of the fourth partial wavelength region received by the plurality of second light receiving elements at the timing other than the predetermined timing.

15. An image capturing method comprising:
image capturing including a plurality of first light receiving elements for receiving light of a first wavelength region and a plurality of second light receiving elements for receiving light of a second wavelength region;
controlling to cause to be generated, from a subject, light of a different spectrum at a different timing for each of the first wavelength region and the second wavelength region;
image generating a first image from a combination that includes at least one of light of a first spectrum from the subject received by the plurality of first light receiving elements at a predetermined timing, light of a second spectrum from the subject received by the plurality of second light receiving elements at the predetermined timing, light of a third spectrum from the subject received by the plurality of first light receiving elements at a timing other than the predetermined timing, and light of a fourth spectrum from the subject received by the plurality of second light receiving elements at the timing other than the predetermined timing, and generating a second image from a combination different from the combination used to generate the first image;
wherein
the controlling includes causing to be generated, from the subject, light of a first partial wavelength region included in the first wavelength region and light of a second partial wavelength region included in the second wavelength region at the predetermined timing, and causing to be generated, from the subject, light of a third partial wavelength region included in the first wavelength region and light of a fourth partial wavelength region included in the second wavelength region at the timing other than the predetermined timing, and
the image generating comprises generating the first image from a combination that includes at least one of light of the first partial wavelength region from the subject received by the plurality of first light receiving elements at the predetermined timing, the light of the third partial wavelength region from the subject received by the plurality of first light receiving elements at the timing other than the predetermined timing, the light of the second partial wavelength region from the subject received by the plurality of second light receiving elements at the predetermined timing, and the light of the fourth partial wavelength region from the subject received by the plurality of second light receiving elements at the timing other than the predetermined timing;
and further comprising:
causing to be emitted, from the subject, light of the first partial wavelength region, the second partial wavelength region, the third partial wavelength region, and the fourth partial wavelength region, wherein
the controlling includes controlling the light emission to emit the light which causes the light of the first partial wavelength region and the light of the second partial wavelength region emitting from the subject at the predetermined timing, and controlling the light emission to emit the light of the third partial wavelength region and the light of the fourth partial wavelength region from the subject at the timing other than the predetermined timing;
wherein
the plurality of first light receiving elements and the plurality of second light receiving elements receive the light emitted after being reflected from an object existing inside a substance,
the first wavelength region that is shorter than the second wavelength region,
the image generating includes the first image based at least on the light of the first partial wavelength region received by the plurality of first light receiving elements at the predetermined timing; and
wherein
the first partial wavelength region is shorter than the third partial wavelength region and the second partial wavelength region is longer than the fourth partial wavelength region, at the predetermined timing, and
the first image represents an image of an object existing at a shallower position from the surface of the substance and an object existing at a deeper position from the surface of the substance, and the image generating includes the first image based at least on the light of the first partial wavelength region received by the plurality of first light receiving elements at the predetermined timing and the light of the second partial wavelength region received by the plurality of second light receiving elements at the predetermined timing.

16. A non-transitory computer readable medium storing thereon a program for an image capturing system, the program causing the image capturing system to function as:
an image capturing section that includes a plurality of first light receiving elements for receiving light of a first wavelength region and a plurality of second light receiving elements for receiving light of a second wavelength region;
a control section that causes to be generated, from a subject, light of a different spectrum at a different timing for each of the first wavelength region and the second wavelength region; and
an image generating section that generates a first image from a combination that includes at least one of light of a first spectrum from the subject received by the plurality of first light receiving elements at a predetermined timing, light of a second spectrum from the subject received by the plurality of second light receiving elements at the predetermined timing, light of a third spectrum from the subject received by the plurality of first light receiving elements at a timing other than the predetermined timing, and light of a fourth spectrum from the subject received by the plurality of second light receiving elements at the timing other than the predetermined timing, and generates a second image from a combination different from the combination used to generate the first image;

wherein the control section causes to be generated, from the subject, light of a first partial wavelength region included in the first wavelength region and light of a second partial wavelength region included in the second wavelength region at the predetermined timing, and causes to be generated, from the subject, light of a third partial wavelength region included in the first wavelength region and light of a fourth partial wavelength region included in the second wavelength region at the timing other than the predetermined timing, and the image generating section generates the first image from a combination that includes at least one of light of the first partial wavelength region from the subject received by the plurality of first light receiving elements at the predetermined timing, the light of the third partial wavelength region from the subject received by the plurality of first light receiving elements at the timing other than the predetermined timing, the light of the second partial wavelength region from the subject received by the plurality of second light receiving elements at the predetermined timing, and the light of the fourth partial wavelength region from the subject received by the plurality of second light receiving elements at the timing other than the predetermined timing; and further comprising:

a light emission section that causes to be emitted, from the subject, light of the first partial wavelength region, the second partial wavelength region, the third partial wavelength region, and the fourth partial wavelength region, wherein the control section controls the light emission section to emit the light which causes the light of the first partial wavelength region and the light of the second partial wavelength region emitting from the subject at the predetermined timing, and controls the light emission section to emit the light of the third partial wavelength region and the light of the fourth partial wavelength region from the subject at the timing other than the predetermined timing;

wherein the plurality of first light receiving elements and the plurality of second light receiving elements receive the light emitted by the light emission section after being reflected from an object existing inside a substance, the first wavelength region that is shorter than the second wavelength region, the image generating section generates the first image based at least on the light of the first partial wavelength region received by the plurality of first light receiving elements at the predetermined timing; and wherein the first partial wavelength region is shorter than the third partial wavelength region and the second partial wavelength region is longer than the fourth partial wavelength region, at the predetermined timing, and the first image represents an image of an object existing at a shallower position from the surface of the substance and an object existing at a deeper position from the surface of the substance, and the image generating section generates the first image based at least on the light of the first partial wavelength region received by the plurality of first light receiving elements at the predetermined timing and the light of the second partial wavelength region received by the plurality of second light receiving elements at the predetermined timing.

* * * * *